(12) United States Patent
Muratoglu et al.

(10) Patent No.: US 9,273,189 B2
(45) Date of Patent: *Mar. 1, 2016

(54) HIGHLY CRYSTALLINE POLYETHYLENE

(71) Applicant: The General Hospital Corporation, Boston, MA (US)

(72) Inventors: Orhun K. Muratoglu, Cambridge, MA (US); Ebru Oral, Newton, MA (US)

(73) Assignee: The General Hospital Corporation, Boston, MA (US)

(*) Notice: Subject to any disclaimer, the term of this patent is extended or adjusted under 35 U.S.C. 154(b) by 153 days.

This patent is subject to a terminal disclaimer.

(21) Appl. No.: 13/799,593

(22) Filed: Mar. 13, 2013

(65) Prior Publication Data

US 2013/0197120 A1    Aug. 1, 2013

Related U.S. Application Data

(63) Continuation of application No. 11/739,300, filed on Apr. 24, 2007, now Pat. No. 8,420,000, which is a continuation of application No. 11/465,509, filed on Aug. 18, 2006, now Pat. No. 8,425,815.

(60) Provisional application No. 60/709,796, filed on Aug. 22, 2005.

(51) Int. Cl.
  *B29C 35/08*     (2006.01)
  *C08J 3/24*      (2006.01)
  (Continued)

(52) U.S. Cl.
  CPC .. *C08J 3/24* (2013.01); *A61L 27/16* (2013.01); *C08F 110/02* (2013.01); *C08J 3/20* (2013.01); *C08J 3/28* (2013.01); *C08K 5/1545* (2013.01); *C08J 7/08* (2013.01); *C08J 2323/06* (2013.01); *C08J 2371/10* (2013.01); *C08J 2377/00* (2013.01); *C08L 23/06* (2013.01); *C08L 2207/068* (2013.01); *Y10T 428/31692* (2015.04)

(58) Field of Classification Search
  CPC ........................................... A61L 27/16
  USPC ........................................... 264/494
  See application file for complete search history.

(56) References Cited

U.S. PATENT DOCUMENTS 5,827,904 A    10/1998   Hahn
5,879,400 A     3/1999   Merrill et al.
(Continued)

FOREIGN PATENT DOCUMENTS

JP    07-502290    3/1995
JP    2003-530957  10/2003
(Continued)

OTHER PUBLICATIONS

Baker et al., Polymer 41(2): 795-808 (2000).
(Continued)

*Primary Examiner* — Michael Pepitone
(74) *Attorney, Agent, or Firm* — Perkins Coie LLP

(57) ABSTRACT

The present invention relates to methods for making highly crystalline polymeric material, for example, highly crystalline cross-linked and not cross-linked ultra-high molecular weight polyethylene (UHMWPE). The invention also provides methods of making additive-doped highly crystalline polymeric material using high pressure and high temperature crystallization processes, medical implants made thereof, and materials used therein.

50 Claims, 18 Drawing Sheets

(51) Int. Cl.
*A61L 27/16* (2006.01)
*C08F 110/02* (2006.01)
*C08J 3/20* (2006.01)
*C08J 3/28* (2006.01)
*C08K 5/1545* (2006.01)
*C08L 23/06* (2006.01)
*B29C 71/02* (2006.01)

(56) References Cited

U.S. PATENT DOCUMENTS

| | | | |
|---|---|---|---|
| 6,448,315 B1 | 9/2002 | Lidgren et al. | |
| 6,517,857 B2 | 2/2003 | Ylänen et al. | |
| 6,562,540 B2 | 5/2003 | Saum et al. | |
| 6,620,198 B2 | 9/2003 | Burstein et al. | |
| 6,641,617 B1 | 11/2003 | Merrill et al. | |
| 6,852,772 B2 | 2/2005 | Muratoglu et al. | |
| 7,431,874 B2 | 10/2008 | Muratoglu et al. | |
| 7,906,064 B2 | 3/2011 | Muratoglu et al. | |
| 8,420,000 B2 * | 4/2013 | Muratoglu et al. | 264/494 |
| 8,425,815 B2 * | 4/2013 | Muratoglu et al. | 264/109 |
| 8,426,486 B2 * | 4/2013 | Muratoglu et al. | 522/157 |
| 8,728,379 B2 * | 5/2014 | Muratoglu et al. | 264/494 |
| 2002/0125614 A1 | 9/2002 | King et al. | |
| 2004/0156879 A1 * | 8/2004 | Muratoglu et al. | 424/423 |
| 2005/0146070 A1 | 7/2005 | Muratoglu et al. | |
| 2007/0265369 A1 | 11/2007 | Muratoglu et al. | |
| 2007/0267030 A1 | 11/2007 | Muratoglu et al. | |
| 2010/0082101 A1 | 4/2010 | Muratoglu et al. | |

FOREIGN PATENT DOCUMENTS

| | | |
|---|---|---|
| WO | WO 93/10953 | 6/1993 |
| WO | WO 97/29793 | 8/1997 |
| WO | WO 99/52474 | 10/1999 |
| WO | WO 01/05337 | 1/2001 |
| WO | WO 01/80778 | 11/2001 |
| WO | WO 03/059220 | 7/2003 |
| WO | WO 04/000159 | 12/2003 |
| WO | WO 2004/064618 | 8/2004 |
| WO | WO 2005/074619 | 8/2005 |

OTHER PUBLICATIONS

Bassett et al., J Appl. Phys. 45(10): 4146-4150 (1974).
Bistolfi et al., 51st Annual Meeting of the Orthopaedic Research Society (Paper No. 0240) Morphological, Tensile and Wear Properties of High Crystallinity Crosslinked UHMWPE.
Collier et al., The Journal of Anthroplasty 11(4): 377-389 (1996).
Kurtz et al., Biomaterials 20(18): 1659-1688 (1999).
McCrum et al., Anelastic and Dielectric Effects in Polymeric Solids, Molecular Theories of Relaxation, pp. 141-145 (1967).
McKellop et al., Journal of Orthopaedic Research 17(2): 157-167 (1999).
Muratoglu et al., The Journal of Arthroplasty 16(2): 149-160 (2001).
Muratoglu et al., Biomaterials 20: 1463-1470 (1999).
Oral et al., 51st Annual Meeting of the Orthopaedic Reserach Society (Poster No: 0988) High-Pressure Crystallized, Irradiated and α-Tocopherol-Stabilized UHMWPE with High Crystallinity, Low Wear and Oxidation.
Oral et al., Biomaterials 26: 6657-6663 (2005).
Parth et al., Journal of Materials Science: Materials in Medicine 13: 917-921 (2002).
Pruitt et al., 50th Annual Meeting of the Orthopaedic Research Society (Poster No: 1471) Fatigue Behavior of Crosslinked UHMWPE with High Crystallinity.
Wolf et al., J. Mat. Sci.: Mat in Med 17: 1341-1347 (2006).
Wolf et al., J. Mat. Sci.: Mat in Med 13: 701-705 (2002).
Wunderlich et al., Journal of Polymer Science Part A-2 Polymer Physics 7(12): 2043-2050 (1969).

* cited by examiner

HIGHLY CRYSTALLINE POLYETHYLENE

This application is a continuation of U.S. application Ser. No. 11/739,300 filed Apr. 24, 2007, now U.S. Pat. No. 8,420,000, which is a continuation of U.S. application Ser. No. 11/465,509 filed Aug. 18, 2006, now U.S. Pat. No. 8,425,815, which claims priority to U.S. Provisional Application No. 60/709,796, filed Aug. 22, 2005. The entire contents of the above-identified applications are hereby incorporated by reference.

FIELD OF THE INVENTION

The present invention relates to methods for making highly crystalline polymeric materials, including highly crystalline oxidation-resistant cross-linked polymeric materials. Methods of crystallizing polymeric materials under high pressure at elevated temperature and materials used therewith also are provided.

BACKGROUND OF THE INVENTION

Cross-linking by irradiation decreases the fatigue strength of UHMWPE. In addition, post-irradiation melting further decreases the fatigue strength of the UHMWPE. Radiation and melting also decrease the yield strength, ultimate tensile strength, toughness and elongation at break of UHMWPE.

Melting in combination with irradiation creates cross-links and facilitates recombination of the residual free radicals trapped mostly in the crystalline regions, which otherwise would cause oxidative embrittlement upon reactions with oxygen. However, cross-linking and the decrease in the crystallinity accompanying post-irradiation melting are thought to be the reasons for the decrease in fatigue strength, yield strength, ultimate tensile strength, toughness and elongation at break of radiation cross-linked and melted UHMWPE. Some or all of these changes in properties limit the use of low wear highly cross-linked UHMWPE to low stress applications. Therefore, a cross-linked UHMWPE with higher crystallinity is desirable for low wear and high fatigue resistance for high stress application that require low wear.

It is, therefore, desirable to reduce the irradiation-created residual free radical concentration in cross-linked UHMWPE without reducing crystallinity, so as to achieve high fatigue resistance for high stress application that require low wear. Alternative methods to melting can be used to prevent the long-term oxidation of irradiated UHMWPE to preserve higher levels of crystallinity and fatigue strength.

The effect of crystallinity on the fatigue strength of conventional UHMWPE is known. Investigators increased the crystallinity of unirradiated UHMWPE by high-pressure crystallization, which increased the fatigue crack propagation resistance of unirradiated UHMWPE by about 25% (Baker et al., Polymer, 2000. 41(2): p. 795-808). Others found that under high pressures (2,000-7,000 bars) and high temperatures (>200° C.), polyethylene grows extended chain crystals and achieves a higher crystallinity level (Wunderlich et al., Journal of Polymer Science Part A-2: Polymer Physics, 1969. 7(12): p. 2043-2050). High pressure crystallization may improve the fatigue strength of irradiated UHMWPE despite no significant changes in ultimate tensile strength (Pruitt et al., 7$^{th}$ World Biomaterials Congress, 2004. p. 538. Bistolfi et al., Transactions, Orthopaedic Research Society, 2005. p. 240) through first melting than pressurizing. The crystallization behavior of not cross-linked or highly cross-linked polyethylene at high pressures through first pressurizing, then heating at the high pressures has not been determined.

Polyethylene undergoes a phase transformation at elevated temperatures and pressures from the orthorhombic to the hexagonal crystalline phase. The hexagonal phase can grow extended chain crystals and result in higher crystallinity in polyethylene. This is believed to be a consequence of less hindered crystallization kinetics in the hexagonal phase compared with the orthorhombic phase. One could further reduce the hindrance on the crystallization kinetics by introducing a plasticizing or a nucleating agent into the polyethylene prior to high-pressure crystallization. The polyethylene can be doped with a plasticizing agent, for example, α-tocopherol or vitamin E, prior to high-pressure crystallization. The doping can be achieved either by blending the polyethylene resin powder with the plasticizing agent and consolidating the blend or by diffusing the plasticizing agent into the consolidated polyethylene. Various processes of doping can be employed as described in U.S. application Ser. No. 10/757,551, filed Jan. 15, 2004, PCT/US/04/00857, filed Jan. 15, 2004, U.S. Provisional Application No. 60/541,073, filed Feb. 3, 2004, and PCT/US2005/003305, filed Feb. 3, 2005, the entireties of which are hereby incorporated by reference.

Reduction in adhesive/abrasive wear of ultra-high molecular weight polyethylene (UHMWPE) components can be achieved by decreasing the large-scale deformation ability of the polymer. Cross-linking by ionizing radiation is generally used for this purpose (see Muratoglu et al., J Arthroplasty, 2001. 16(2): p. 149-160; Muratoglu et al., Biomaterials, 1999. 20(16): p. 1463-1470; and McKellop et al., J Orthop Res, 1999. 17(2): p. 157-167) with a concomitant decrease in strength (Oral et al., Biomaterials, 2005).

In order to increase the strength of UHMWPE, high pressure crystallization (HPC) of UHMWPE has been proposed (see Bistolfi et al., Transactions of the Orthopaedic Research Society, 2005. 240; Oral et al. Transactions of the Orthopaedic Research Society, 2005. p. 988, U.S. Provisional Application No. 60/541,073, filed Feb. 3, 2004, and PCT/US2005/003305, filed Feb. 3, 2005). High pressure crystallization of unirradiated GUR1050 UHMWPE at above 160° C. and 300 MPa yielded an approximately 70% crystalline UHMWPE, compared to 50-60% for conventional UHMWPE. This is due to a phase transition of the UHMWPE crystals from the orthorhombic to the hexagonal phase at high temperatures and pressures as discussed above. In the hexagonal phase crystals grow to larger sizes and crystallinity increases (see Bassett et al., J Appl. Phys., 1974. 45(10): p. 4146-4150).

While high pressure crystallization can be used to increase the strength of UHMWPE, it has been shown to decrease the wear resistance of unirradiated UHMWPE (see Bistolfi et al., Transactions, Orthopaedic Research Society, 2005. p. 240). It appears that the decrease in ductility accompanying high pressure crystallization may adversely affect the wear resistance.

SUMMARY OF THE INVENTION

The present invention relates generally to methods of making highly crystalline polymeric material, preferably the cross-linked material has higher crystallinity than obtainable with previous methodologies. More specifically, the invention relates to methods of making highly crystalline cross-linked UHMWPE and subsequently treating the UHMWPE to increase its oxidation resistance. Also, the invention relates to methods of crystallizing cross-linked ultra-high molecular weight polyethylene (UHMWPE) under high pressure at elevated temperature in the hexagonal phase, whereby extended chain crystals are present and high crystallinity are achieved. Also, the invention relates to methods of crystallizing cross-linked ultra-high molecular weight polyethylene (UHMWPE) under high pressure at elevated temperature in the hexagonal phase, whereby extended chain crystals are present and high crystallinity are achieved followed by treating the UHMWPE to increase its oxidation resistance. The invention also relates to methods of crystallizing polymeric materials including cross-linked and not cross-linked ultra-high molecular weight polyethylene (UHMWPE) under high pressure at elevated temperature in the hexagonal phase where high crystallinity is achieved. Also the invention relates to methods of increasing the crystallinity of oxidation-resistant cross-linked and not cross-linked UHMWPE by high-pressure crystallization. The invention also relates to methods of crystallizing blends of polymeric materials including ultra-high molecular weight polyethylene (UHMWPE) with additives such as a plasticizing agent or an antioxidant under high pressure at elevated temperature in the hexagonal phase where high crystallinity is achieved.

The process comprises steps of crystallizing polyethylene under high pressure at elevated temperature, irradiating at different temperatures below or above the melt to control the amount of amorphous, folded and extended chain crystals during cross-linking. This invention also relates to processes to increase oxidation resistance where an antioxidant is incorporated into polyethylene, or a cross-linked polyethylene is annealed, or a high pressure and high temperatures are applied to the cross-linked polyethylene. The processes can be used separately or together in various orders in accordance with the teachings herein and the skill in the art. All ranges set forth herein in the summary and description of the invention include all numbers or values thereabout or therebetween of the numbers of the range. The ranges of the invention expressly denominate and set forth all integers and fractional values in the range.

In one aspect, the invention provides methods of making a highly crystalline cross-linked polymeric material comprising: a) irradiating a polymeric material with ionizing radiation, thereby forming a cross-linked polymeric material; b) pressurizing the cross-linked polymeric material under at least 10-1000 MPa; c) heating the pressurized cross-linked polymeric material to a temperature below the melt of the pressurized cross-linked material; d) holding at this temperature and pressure; e) cooling the heated cross-linked polymeric material to about room temperature; and f) releasing the pressure to an atmospheric pressure level, thereby forming a highly crystalline cross-linked polymeric material.

In another aspect, the invention provides methods of making highly crystalline blend of polymeric material comprising: a) blending a polymeric material with an additive; b) consolidating the blend; c) pressurizing the blended polymeric material under at least 10-1000 MPa; d) heating the pressurized blended polymeric material to a temperature below the melt of the pressurized blended material; e) holding at this temperature and pressure; f) cooling the heated blended polymeric material to about room temperature; and g) releasing the pressure to an atmospheric pressure level, thereby forming oxidation resistant highly crystalline blend of polymeric material.

In another aspect, the invention provides methods of making oxidation resistant highly crystalline blend of polymeric material comprising: a) blending a polymeric material with an antioxidant; b) consolidating the blend; c) pressurizing the blended polymeric material under at least 10-1000 MPa; d) heating the pressurized blended polymeric material to a temperature below the melt of the pressurized blended material; e) holding at this temperature and pressure; f) cooling the heated blended polymeric material to about room temperature; and g) releasing the pressure to an atmospheric pressure level, thereby forming oxidation resistant highly crystalline blend of polymeric material.

In another aspect, the invention provides methods of making highly crystalline blend of polymeric material comprising: a) blending a polymeric material with an additive; b) consolidating the blend; c) heating the blended polymeric material to a temperature above the melt; d) pressurizing the heated blended polymeric material under at least 10-1000 MPa; e) holding at this temperature and pressure; f) cooling the heated blended polymeric material to about room temperature; and g) releasing the pressure to an atmospheric pressure level, thereby forming highly crystalline blend of polymeric material.

In another aspect, the invention provides methods of making oxidation resistant highly crystalline blend of polymeric material comprising: a) blending a polymeric material with an antioxidant; b) consolidating the blend; c) heating the blended polymeric material to a temperature above the melt; d) pressurizing the heated blended polymeric material under at least 10-1000 MPa; e) holding at this temperature and pressure; f) cooling the heated blended polymeric material to about room temperature; and g) releasing the pressure to an atmospheric pressure level, thereby forming oxidation resistant highly crystalline blend of polymeric material.

In another aspect, the invention provides methods of making oxidation resistant highly crystalline cross-linked polymeric material comprising: a) irradiating the polymeric material with ionizing radiation, thereby forming a cross-linked polymeric material; b) heating the cross-linked polymeric material to a temperature above the melt; c) pressurizing the cross-linked polymeric material under at least 10-1000 MPa; d) holding at this temperature and pressure; e) cooling the heated cross-linked polymeric material to about room temperature; f) releasing the pressure to an atmospheric pressure level, thereby forming a highly crystalline cross-linked polymeric material; g) doping the highly crystalline cross-linked polymeric material with an antioxidant by diffusion; and h) annealing the antioxidant-doped highly crystalline cross-linked polymeric material at a temperature below the melting point of the antioxidant-doped cross-linked highly crystalline polymeric material, thereby forming oxidation resistant highly crystalline cross-linked polymeric material.

In another aspect, the invention provides methods of making oxidation resistant highly crystalline cross-linked polymeric material comprising: a) irradiating the polymeric material with ionizing radiation, thereby forming a cross-linked polymeric material; b) pressurizing the cross-linked polymeric material under at least 10-1000 MPa; c) heating the pressurized cross-linked polymeric material to a temperature below the melting point of the pressurized cross-linked polymeric material; d) holding at this temperature and pressure; e) cooling the heated cross-linked polymeric material to about room temperature; f) releasing the pressure to an atmospheric pressure level, thereby forming a highly crystalline cross-linked polymeric material; g) doping the highly crystalline cross-linked polymeric material with an antioxidant by diffusion; and h) annealing the antioxidant-doped highly crystalline cross-linked polymeric material at a temperature below the melting point of the polymeric material, thereby forming oxidation resistant highly crystalline cross-linked polymeric material.

In another aspect, the invention provides methods of making a highly crystalline cross-linked polymeric material comprising the steps of: a) heating the polymeric material to a temperature above the melt; b) pressurizing the polymeric material under at least 10-1000 MPa; c) holding at this temperature and pressure; d) cooling the heated polymeric material to about room temperature; e) releasing the pressure to an atmospheric pressure level, thereby forming a highly crystalline polymeric material; f) irradiating the highly crystalline polymeric material melt with ionizing radiation, thereby forming a cross-linked highly crystalline polymeric material; and g) annealing the cross-linked highly crystalline polymeric material below the melt.

In another aspect, the invention provides methods of making a highly crystalline cross-linked polymeric material comprising the steps of: a) heating the polymeric material to a temperature above the melt; b) pressurizing the polymeric material under at least 10-1000 MPa; c) holding at this temperature and pressure; d) cooling the heated polymeric material to about room temperature; e) releasing the pressure to an atmospheric pressure level, thereby forming a highly crystalline polymeric material; f) irradiating the highly crystalline polymeric material melt with ionizing radiation, thereby forming a cross-linked highly crystalline polymeric material; and g) heating the cross-linked highly crystalline polymeric material above the melting point.

In another aspect, the invention provides methods of making highly crystalline polymeric material comprising: a) doping the polymeric material with an additive by diffusion; b) heating the polymeric material to a temperature of above the melting point of the polymeric material; c) pressuring the heated polymeric material under at least 10-1000 MPa; d) holding at this pressure and temperature; e) cooling the heated polymeric material to about room temperature; and f) releasing the pressure to about an atmospheric pressure level, thereby forming a highly crystalline polymeric material.

In another aspect, the invention provides methods of making highly crystalline polymeric material comprising: a) doping the polymeric material with an additive by diffusion; b) pressuring the polymeric material under at least 10-1000 MPa; c) heating the pressurized polymeric material to a temperature of above 100° C. to below the melt of the pressurized polymeric material; d) holding at this pressure and temperature; e) cooling the heated polymeric material to about room temperature; and f) releasing the pressure to about an atmospheric pressure level, thereby forming a highly crystalline polymeric material.

In another aspect, the invention provides methods of making cross-linked highly crystalline polymeric material comprising: a) doping the polymeric material with an additive by diffusion; b) heating the polymeric material to a temperature of above the melting point of the polymeric material; c) pressuring the heated polymeric material under at least 10-1000 MPa; d) holding at this pressure and temperature; e) cooling the heated polymeric material to about room temperature; f) releasing the pressure to about an atmospheric pressure level, thereby forming a highly crystalline polymeric material; and g) irradiating the highly crystalline polymeric material with ionizing radiation, thereby forming a highly crystalline cross-linked polymeric material.

In another aspect, the invention provides methods of making cross-linked highly crystalline polymeric material comprising: a) doping the polymeric material with an additive by diffusion; b) pressuring the polymeric material under at least 10-1000 MPa; c) heating the pressurized polymeric material to a temperature of above 100° C. to below the melt of the pressurized polymeric material; d) holding at this pressure and temperature; e) cooling the heated polymeric material to about room temperature; f) releasing the pressure to about an atmospheric pressure level, thereby forming a highly crystalline polymeric material; and g) irradiating the highly crystalline polymeric material with ionizing radiation, thereby forming a highly crystalline cross-linked polymeric material.

In another aspect, the invention provides methods of making highly crystalline polymeric material comprising: a) irradiating the polymeric material with ionizing radiation, thereby forming a cross-linked polymeric material; b) doping the cross-linked polymeric material with an additive by diffusion; c) heating the crosslinked polymeric material to a temperature of above the melting point of the crosslinked polymeric material; d) pressuring the heated crosslinked polymeric material under at least 10-1000 MPa; e) holding at this pressure and temperature; f) cooling the heated crosslinked polymeric material to about room temperature; and g) releasing the pressure to about an atmospheric pressure level, thereby forming a highly crystalline crosslinked polymeric material.

In another aspect, the invention provides methods of making cross-linked highly crystalline polymeric material comprising: a) irradiating the polymeric material with ionizing radiation, thereby forming a cross-linked polymeric material; b) doping the cross-linked polymeric material with an additive by diffusion; b) pressuring the cross-linked polymeric material under at least 10-1000 MPa; c) heating the pressurized cross-linked polymeric material to a temperature of above 100° C. to below the melt of the pressurized cross-linked polymeric material; d) holding at this pressure and temperature; e) cooling the heated cross-linked polymeric material to about room temperature; and f) releasing the pressure to about an atmospheric pressure level, thereby forming a highly crystalline cross-linked polymeric material.

In another aspect, the invention provides methods of making highly crystalline polymeric material comprising: a) doping the polymeric material with an additive by diffusion; b) annealing the polymeric material below or above the melt; c) heating the polymeric material to a temperature of above the melting point of the polymeric material; d) pressuring the heated polymeric material under at least 10-1000 MPa; e) holding at this pressure and temperature; f) cooling the heated polymeric material to about room temperature; and g) releasing the pressure to about an atmospheric pressure level, thereby forming a highly crystalline polymeric material.

In another aspect, the invention provides methods of making highly crystalline polymeric material comprising: a) doping the polymeric material with an additive by diffusion; b) annealing the polymeric material below or above the melt; c) pressuring the polymeric material under at least 10-1000 MPa; d) heating the pressurized polymeric material to a temperature of above 100° C. to below the melt of the pressurized polymeric material; e) holding at this pressure and temperature; f) cooling the heated polymeric material to about room temperature; and g) releasing the pressure to about an atmospheric pressure level, thereby forming a highly crystalline polymeric material.

In another aspect, the invention provides methods of making highly crystalline cross-linked polymeric material comprising: a) doping the polymeric material with an additive by diffusion; b) annealing the polymeric material below or above the melt; c) heating the polymeric material to a temperature of above the melting point of the polymeric material; d) pressuring the heated polymeric material under at least 10-1000 MPa; e) holding at this pressure and temperature; f) cooling the heated polymeric material to about room temperature; g) releasing the pressure to about an atmospheric pressure level, thereby forming a highly crystalline polymeric material; and h) irradiating the highly crystalline polymeric material with ionizing radiation, thereby forming a cross-linked highly crystalline polymeric material.

In another aspect, the invention provides methods of making highly crystalline cross-linked polymeric material comprising: a) doping the polymeric material with an additive by diffusion; b) annealing the polymeric material below or above the melt; c) pressuring the polymeric material under at least 10-1000 MPa; d) heating the pressurized polymeric material to a temperature of above 100° C. to below the melt of the pressurized polymeric material; e) holding at this pressure and temperature; f) cooling the heated polymeric material to about room temperature; g) releasing the pressure to about an atmospheric pressure level, thereby forming a highly crystalline polymeric material; and h) irradiating the highly crystalline polymeric material with ionizing radiation, thereby forming a cross-linked highly crystalline polymeric material.

In another aspect, the invention provides methods of making highly crystalline polymeric material comprising: a) irradiating the polymeric material with ionizing radiation, thereby forming a cross-linked polymeric material; b) doping the cross-linked polymeric material with an additive by diffusion; c) annealing the cross-linked polymeric material below or above the melt; d) heating the crosslinked polymeric material to a temperature of above the melting point of the crosslinked polymeric material; e) pressuring the heated crosslinked polymeric material under at least 10-1000 MPa; f) holding at this pressure and temperature; g) cooling the heated crosslinked polymeric material to about room temperature; and h) releasing the pressure to about an atmospheric pressure level, thereby forming a highly crystalline crosslinked polymeric material.

In another aspect, the invention provides methods of making cross-linked highly crystalline polymeric material comprising: a) irradiating the polymeric material with ionizing radiation, thereby forming a cross-linked polymeric material; b) doping the cross-linked polymeric material with an additive by diffusion; c) annealing the cross-linked polymeric material below or above the melt; d) pressuring the cross-linked polymeric material under at least 10-1000 MPa; e) heating the pressurized cross-linked polymeric material to a temperature of above 100° C. to below the melt of the pressurized cross-linked polymeric material; f) holding at this pressure and temperature; g) cooling the heated cross-linked polymeric material to about room temperature; and h) releasing the pressure to about an atmospheric pressure level, thereby forming a highly crystalline cross-linked polymeric material.

In another aspect, the invention provides irradiated or unirradiated blend of UHMWPE with an additive, wherein the blend of the UHMWPE and additive is machined to form a finished product, for example, an article, an implant, or a medical prosthesis and the like, and wherein the finished product is high pressure crystallized. High pressure crystallization is carried out by heating to a temperature above the melting point of the irradiated or unirradiated UHMWPE at ambient pressure, pressurizing to at least about 10-1000 MPa, preferably at least about 150 MPa, more preferably at least about 250 MPa, heating to a temperature above the melting point, cooling to about room temperature and releasing the pressure. High pressure crystallization also can be carried out by pressurizing to at least about 10-1000 MPa, preferably at least about 150 MPa, more preferably at least about 250 MPa, heating to a temperature above the melting point of the irradiated or unirradiated UHMWPE at ambient pressure and below the melting point of the pressurized irradiated or unirradiated UHMWPE, cooling to about room temperature, and releasing the pressure. The finished product can be packaged and sterilized.

In another aspect, the invention provides UHMWPE incorporated with an additive by either doping by diffusion or by blending with powder and consolidation of the blend, wherein the UHMWPE is high pressure crystallized. High pressure crystallization is carried out by heating to a temperature above the melting point of the irradiated or unirradiated UHMWPE at ambient pressure, pressurizing to at least about 10-1000 MPa, preferably at least about 150 MPa, more preferably at least about 250 MPa, heating to a temperature above the melting point, cooling to about room temperature and releasing the pressure. High pressure crystallization also can be carried out by pressurizing to at least about 10-1000 MPa, preferably at least about 150 MPa, more preferably at least about 250 MPa, heating to a temperature above the melting point of the irradiated or unirradiated UHMWPE at ambient pressure and below the melting point of the pressurized irradiated or unirradiated UHMWPE, cooling to about room temperature, and releasing the pressure. A finished product can be machined. The finished product can be packaged and sterilized.

In another aspect, the invention provides cross-linked UHMWPE incorporated with an additive by either doping by diffusion or by blending with powder and consolidation of the blend, wherein the UHMWPE is high pressure crystallized and irradiated. In another aspect, the invention provides cross-linked UHMWPE incorporated with an additive by either doping by diffusion or by blending with powder and consolidation of the blend, wherein the UHMWPE is irradiated and high pressure crystallized.

Unless otherwise defined, all technical and scientific terms used herein in their various grammatical forms have the same meaning as commonly understood by one of ordinary skill in the art to which this invention belongs. Although methods and materials similar to those described herein can be used in the practice or testing of the present invention, the preferred methods and materials are described below. In case of conflict, the present specification, including definitions, will control. In addition, the materials, methods, and examples are illustrative only and are not limiting.

Further features, objects, and advantages of the present invention are apparent in the claims and the detailed description that follows. It should be understood, however, that the detailed description and the specific examples, while indicating preferred aspects of the invention, are given by way of illustration only, since various changes and modifications within the spirit and scope of the invention will become apparent to those skilled in the art from this detailed description.

DETAILED DESCRIPTION OF THE INVENTION

Figure 1A:
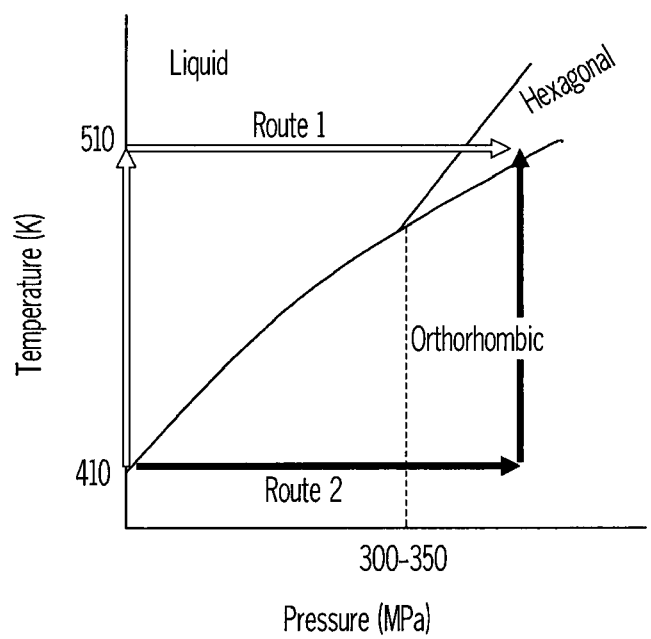
FIG. 1A shows schematically the high-pressure crystallization ("HPC") process and phases of polyethylene under various temperature and pressure conditions.

The invention provides methods of making highly crystalline cross-linked and not cross-linked polymeric material, medical implants made thereof, which comprise medical devices, including permanent and non-permanent medical devices. The invention also provides methods of making oxidation resistant highly crystalline cross-linked and not cross-linked polymeric material and medical implants made thereof, including permanent and non-permanent medical devices. The invention pertains to methods of crystallizing polyethylene, such as UHMWPE, under high pressure at elevated temperature, irradiating at different temperatures, doping the cross-linked polyethylene with an antioxidant. The invention also pertains to methods of blending polyethylene with an additive, such as Vitamin E, crystallizing the blend, irradiating at different temperatures including below or above the melting point of polyethylene under normal or pressured conditions. The invention also pertains to methods of incorporating polyethylene with an additive, such as Vitamin E, and crystallizing the additive-incorporated polymeric material.

Wear resistance in UHMWPE is achieved through a decrease in its large strain deformation ability. Cross-linking is a means of achieving a decrease in large-strain deformation by limiting the mobility of the polymer chains during deformation. While high pressure crystallization (HPC) can be used to increase the strength of UHMWPE, it may adversely affect the wear resistance, presumably due to an increase in stiffness. Therefore, to counteract this, according to one aspect of the invention, a plasticizing agent is used in UHMWPE during high pressure crystallization. The use of a plasticizing agent, such as Vitamin E, during the high pressure crystallization counteracts the decrease in mobility of the chains accompanying the increase in crystallinity obtained by high pressure crystallization. Therefore, incorporation of a plasticizing agent decreases the wear rate of high pressure crystallized UHMWPE and results in higher crystallinity and higher strength. This finding is a paradigm shift in that the reduction in wear need not be achieved by cross-linking and need not be accompanied by a reduction in strength.

Incorporation of a plasticizing agent, such as vitamin E, into UHMWPE can be achieved in different ways, for example, a) by blending with UHMWPE powder and consolidation of the plasticizing agent and UHMWPE; and b) by diffusion of the plasticizing agent into consolidated solid stock, preform or a finished product made of UHMWPE. In order to increase the uniformity of the plasticizing agent in the UHMWPE, the UHMWPE is doped by diffusion followed by annealing at a temperature below or above the melt at ambient pressure or under pressure.

Polyethylene is a semi-crystalline material (55-60%) and contains folded chain crystals when crystallized from the melt under ambient pressures. The majority of the crystals are in the orthorhombic phase with lattice dimensions of 7.42, 4.95, and 2.55 Å for a, b and c dimensions, respectively. The unit cell axes are at 90° to each other. Deformation gives rise to the monoclinic phase with lattice dimensions of 8.09, 4.79, and 2.55 Å. In the hexagonal phase, which is only encountered at pressures in excess of 300 MPa (see FIGS. 1A-1W, for example), the unit cell dimensions become 8.42, 4.56, and <2.55 Å. In this phase, the individual chain stems are rotated at random phase angles with respect to each other allowing for chains to slide past each other to form a densely packed structure. The crystals in this phase are termed the 'Extended Chain Crystals' (ECC) because the dense packing allows the crystals to grow to a larger extent than folded chain crystals.

It is known that the crystallinity of not cross-linked UHMWPE can be increased by high pressure and high temperature crystallization. For instance, when crystallized not cross-linked UHMWPE at pressures above 300 MPa and 160° C. to obtain the hexagonal phase transition, the peak melting point of the crystals, as determined by differential scanning calorimetry (DSC), shifted to higher temperatures and the overall crystallinity increased. Not cross-linked high pressure crystallized polyethylene with high crystallinity appeared to have higher fatigue resistance as a function of increasing crystallinity (see Baker et al., *Polymer,* 2000. 41(2): p. 795-808). Therefore, an object of the invention was to achieve a wear resistant highly crystalline polyethylene (with >51% crystallinity) with good fatigue and oxidation resistance.

High pressure crystallization is generally referred to as all of the methods of allowing the formation of extended chain crystals in the hexagonal phase. This transformation can be done by several different methods. The first is by heating to a temperature above the melting point of the polyethylene at ambient pressure, then pressurizing so that the sample is in the melt during the pressurization until the conditions are met for the melt-to-hexagonal transition to occur. Alternatively, stepwise heating and pressurization is preformed such that the sample is not always in the melt until close to the hexagonal phase. The sample heating and pressurization can be done in a variety of manners such that when the hexagonal phase transformation occurs, the UHMWPE does not have a substantial amount of preformed crystals and is considered in the melt phase.

Once the conditions are met for the hexagonal phase to be achieved and the extended chain crystals are formed, the sample cannot be allowed to completely melt because the desired crystalline structure would be lost. Therefore, any cooling and depressurization scheme allowing the sample to stay in the hexagonal or orthorhombic regions is used. For example, a sample high pressure crystallized at 200° C. and 380 MPa (55,000 psi) is cooled down to approximately below the melting point of polyethylene at room temperature (about 135-140° C.), then the pressure is released. Alternatively, a stepwise cooling and depressurization method is used as long as the sample does not melt substantially.

The ratio of orthorhombic to hexagonal crystals may be dependent on the time spent in the hexagonal phase and whether or not the sample has melted during the cool down. If a sample is fully crystallized in the hexagonal phase, is cooled down and/or depressurized to a pressure such that it encounters the melt phase partially or completely, and solely decreasing the temperature at the new pressure would not cause the sample to be in the hexagonal phase then some or all of the crystals would be converted to orthorhombic crystals when the sample is further cooled down and depressurized.

High toughness and high fatigue strength of polymers are attributed to energy absorbing mechanisms such as cavitation and plastic deformation. The major energy absorbing mechanism in polyethylene is the plastic deformation of the crystalline domains (crystal plasticity), which depends on ductility and crystallinity. Cross-linking polyethylene with high dose levels of irradiation drastically reduces the mobility of the chains, hence reducing the overall ductility. Melting in the presence of cross-links limits the ability of the chains to reorder and hence decreases the crystallinity of polyethylene. The combination of these two factors, namely reduced chain mobility and reduced crystallinity, reduces cross-linked and melted polyethylene's fatigue resistance.

According to the invention, highly crystalline wear-resistant polyethylene can be obtained following various processes and steps, as described below, for example:

1. Incorporating a plasticizing agent into unirradiated or irradiated polyethylene by either one of the following methods:
   A. Blending with plasticizing agent and consolidating;
   B. Doping with plasticizing agent by diffusion, and annealing at a temperature above or below the melt;
2. High pressure crystallized (HPC) the polyethylene using either Route I or Route II:
   A. Route I: Heat to the desired temperature, for example, above the melt (for example, about 140° C., about 160° C., about 180° C., about 200° C., about 250° C., or about 300° C.); then pressurize; then hold pressure at about the same pressure, for one minute to a day or more, preferably about 0.5 hours to 12 hours, more preferably 1 to 6 hours; then release the pressure (pressure has to be released after cooling down to room temperature to avoid melting of the crystals achieved under high pressure).
   B. Route II: Pressurize to the desired pressure; then heat to the desired temperature, for example, below the melt of pressurized polyethylene (for example, about 150° C., about 160° C., about 180° C., about 195° C., about 225° C., about 300° C., and about 320° C.); then hold pressure at about the same pressure, for one minute to a day or more, preferably about 0.5 hours to 12 hours, more preferably 1 to 6 hours; then cool to room temperature; then release the pressure (pressure has to be released after cooling down to room temperature to avoid melting of the crystals achieved under high pressure).

Figure 2:
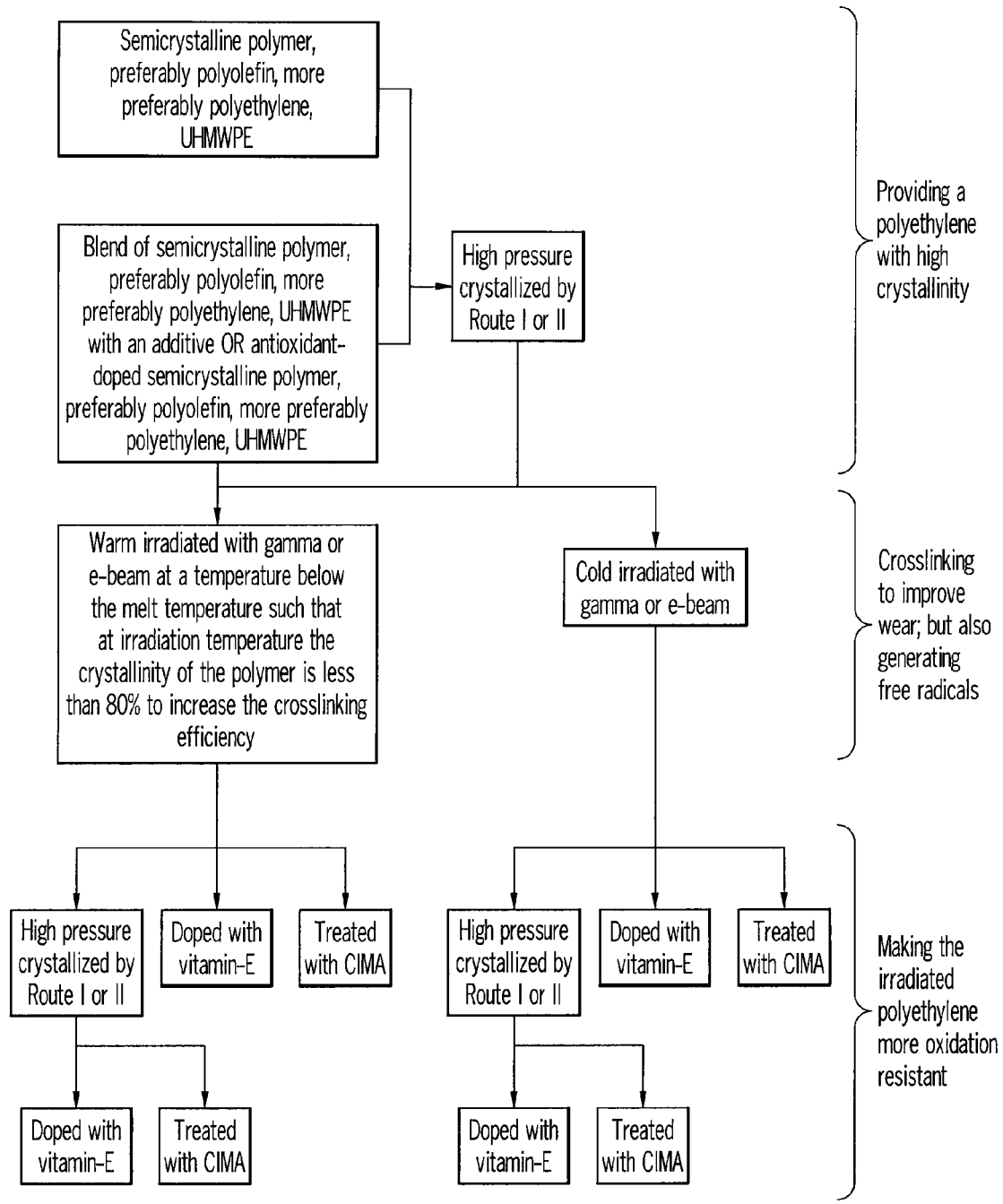
FIG. 2 schematically shows various steps and methods of making highly crystalline oxidation-resistant cross-linked polymeric material.

According to the invention, highly crystalline cross-linked oxidation-resistant polyethylene can be obtained following various processes and steps (see FIG. 2, for example), as described below, for example:

1, High pressure crystallized (HPC) unirradiated and not cross-linked polyethylene using either Route I or Route II:
   A. Route I: Heat to the desired temperature, for example, above the melt (for example, about 140° C., about 160° C., about 180° C., about 200° C., about 250° C., or about 300° C.); then pressurize; then hold pressure at about the same pressure, for one minute to a day or more, preferably about 0.5 hours to 12 hours, more preferably 1 to 6 hours; then release the pressure (pressure has to be released after cooling down to room temperature to avoid melting of the crystals achieved under high pressure).
   B. Route II: Pressurize to the desired pressure; then heat to the desired temperature, for example, below the melt of pressurized polyethylene (for example, about 150° C., about 160° C., about 180° C., about 195° C., about 225° C., about 300° C., and about 320° C.); then hold pressure at about the same pressure, for one minute to a day or more, preferably about 0.5 hours to 12 hours, more preferably 1 to 6 hours; then cool to room temperature; then release the pressure (pressure has to be released after cooling down to room temperature to avoid melting of the crystals achieved under high pressure).
2. Then irradiate the high-pressure crystallized (HPC) polyethylene using either cold or warm irradiation:
   A. Cold Irradiation (CI): irradiate at between about room temperature and 90° C. using either e-beam or gamma radiation. If the crystallinity of the HPC-polyethylene is too high, there may not be enough amorphous polyethylene available for cross-linking. Therefore, it may require higher than usual dose levels, that is the dose levels required for polyethylene crystallized without high-pressure (as described herein, for example, usual dose levels of 75 kGy or 100 kGy), to achieve a desired wear resistance or crosslink density.
   B. Warm Irradiation (WI): irradiate at between about 90° C. and the peak melting point of HPC-polyethylene, which is generally around 145° C. The temperature of irradiation can be adjusted to achieve a desired extent of amorphous polyethylene during irradiation.
3. Then treat the irradiated HPC-polyethylene (1-HPC) by either one of the following methods or a combination thereof:
   A. Repeat the high-pressure crystallization following Route I or Route II, as described above.
   B. Dope with an antioxidant, such as vitamin E, which can be done by various ways, for example,
      i. machine the final product, soak in an antioxidant, such as a vitamin E solution, at between room temperature and boiling point of vitamin E solution; then wash, package and sterilize with either gas plasma, ethylene oxide, or ionizing radiation, such as gamma either in air or in inert gas.
      ii. soak highly crystalline polymeric material in an antioxidant, such as a vitamin E solution, at between room temperature and boiling point of vitamin E solution; machine medical implant, then wash, package and irradiate packaged medical implant to cross-link and sterilize.
   C. Treat with a CIMA (Cold Irradiation and Mechanically Annealed) method, for example,
      i. heat to a temperature between 90° C. and peak melting point of I-HPC, deform under compression to a compression ratio of above 2.5, hold deformation and cool to room temperature, anneal at a temperature between 90° C. and peak melting point of I-HPC, machine the final product, package and sterilize, preferably sterilize with ethylene oxide or gas plasma. CIMA methods can be applied as described in US Patent publication 20030149125 (U.S. application Ser. No. 10/252,582), filed Sep. 24, 2002, the entirety of which is hereby incorporated by reference.

In one aspect of the invention, the polymeric material is heated to a temperature above the melting point, for example, about 140° C., about 160° C., about 180° C., about 200° C., about 250° C., or about 300° C. during the Route I high pressure crystallization.

In another aspect, the polymeric material is heated to a temperature below the melting point of the pressurized polymeric material, for example, about 150° C., about 160° C., about 180° C., about 195° C., about 225° C., about 300° C., and about 320° C. during the Route II high pressure crystallization.

An antioxidant, which is compatible with lipophilic polyethylene, blends well with and protects irradiated polyethylene against oxidation, at radiation doses as high as 100 kGy. Moreover, antioxidant was found not to interfere with crosslinking of polyethylene, when diffused after irradiation. Therefore, cross-linked polyethylene diffused with antioxidant after irradiation showed wear rates comparable to contemporary cross-linked and melted polyethylenes. Mechanical deformation at temperatures below the melt also is an alternative approach of removing residual free radicals from irradiated polyethylene without melting.

The present invention also provides methods of crystallizing a blend of polymer with an additive under a high pressure and high temperatures and irradiating thus formed highly crystalline blend to obtain a highly crystalline, cross-linked blend of polymer and the additive. The present invention also provides methods of crystallizing a blend of polymer with additive, which is also an antioxidant, under a high pressure and high temperatures and irradiating thus formed highly crystalline blend to obtain a highly crystalline, cross-linked oxidation-resistant blend of polymer and an additive, which is also an antioxidant.

The present invention also provides methods of improving the oxidation resistance of highly crystalline cross-linked UHMWPE without melting. Melting of the highly crystalline UHMWPE will eliminate the ECC and reduce the crystallinity of the polymer. Therefore, the present invention provides the methods that use antioxidant or mechanical deformation below the melting point. According to the invention, improvement of oxidation resistance can be achieved either by doping with an antioxidant as described herein or by mechanical deformation methods. The mechanical deformation is used after irradiation to reduce the population of residual free radicals without melting the polymer, for example, uniaxially compressing to a compression ratio of at least 2.0 below the melting point (for example, less than about 150° C.) is utilized to reduce the residual free radical concentration. According to the invention, orientation and some of the thermal stresses that can persist following the mechanical deformation are reduced by further annealing at an elevated temperature below the melting point and cooling down. Following annealing, it may be desirable to cool down the polyethylene at slow enough cooling rate (for example, at about 10° C./hour) so as to minimize thermal stresses.

As described herein, it is demonstrated that mechanical deformation can eliminate residual free radicals in a radiation cross-linked UHMWPE. The invention also provides that one can first deform UHMWPE to a new shape either at solid- or at molten-state, for example, by compression. According to a process of the invention, mechanical deformation of UHMWPE when conducted at a molten-state, the polymer is crystallized under load to maintain the new deformed shape. Following the deformation step, the deformed UHMWPE sample is irradiated at a temperature below the melting point to crosslink, which generates residual free radicals. To reduce or eliminate these free radicals, the irradiated polymer specimen is heated to a temperature below the melting point of the deformed and irradiated polyethylene (for example, up to about 150° C.) to allow for the shape memory to partially recover the original shape. Generally, it is expected to recover about 80-90% of the original shape. During this recovery, the crystals undergo motion, which can help the free radical recombination and elimination. The above process is termed as a 'reverse-IBMA'. The reverse-IBMA (reverse-irradiation below the melt and mechanical annealing) technology can be a suitable process in terms of bringing the technology to large-scale production of UHMWPE-based medical devices.

In one aspect, the invention discloses medical implants, including permanent and non-permanent medical devices, comprising polymeric material having high crosslink density, high crystallinity, wear and oxidation resistance comparable with a highly cross-linked and melted polyethylene with fatigue resistance above highly cross-linked and melted polyethylene.

Medical implants, as disclosed herein can be obtained by various processes disclosed herein, for example, consolidating polymeric material; crystallizing the consolidated polymeric material under a high temperature, such as at above 150° C. and at a high pressure, such as at above 10-1000 MPa (for example, at least about 150 MPa, 200 MPa, 250 MPa, 300 MPa, 310 MPa, 320 MPa, 380 MPa, 400 MPa, or 450 MPa), preferably at least about 150 MPa, more preferably at least about 250 MPa, subsequently, cooling down to room temperature followed by reducing the pressure to ambient, subsequently heating and holding the high pressure crystallized polymeric material at a certain temperature, such as at below 150° C., so as to achieve partly amorphous polyethylene; irradiating by ionizing radiation to a dose of more than 1 kGy, such as about 25-400 kGy or more, preferably to above about 75 kGy, more preferably about 100 kGy; yet more preferably about 150 kGy; increasing the oxidation resistance by either doping with an antioxidant or decreasing the concentration of residual free radicals, for example, by mechanical deformation and annealing and/or crystallizing under high pressure and temperature.

Crystallization under high pressure is done by first melting the polyethylene at low pressure, subsequently pressurizing to above 10-1000 MPa (for example, at least about 150 MPa, 200 MPa, 250 MPa, 300 MPa, 310 MPa, 320 MPa, 380 MPa, 400 MPa, or 450 MPa), preferably at least about 150 MPa, more preferably at least about 250 MPa, and cooling to about room temperature; or by first pressurizing to above 10-1000 MPa (for example, at least about 150 MPa, 200 MPa, 250 MPa, 300 MPa, 310 MPa, 320 MPa, 380 MPa, 400 MPa, or 450 MPa), preferably at least about 150 MPa, more preferably at least about 250 MPa, then increasing the temperature until orthorhombic to hexagonal phase transition occurs, then cooling down and depressurizing.

The holding time in the melt, the holding time under pressure, the ultimate temperature and pressure and the cooling rate can be changed to obtain the highest crystallinity and a roughly equal amount of extended and folded chain crystals.

The temperature at which the folded chain crystals of the high pressure crystallized polyethylene are melted and the holding time at the temperature can be changed to obtain a desired ratio of extended to folded chain crystals and amorphous content.

Irradiation cross-links the high pressure crystallized polyethylene and provides wear resistance. Irradiation can be done at room temperature or at elevated temperatures below the melting point of polyethylene. Irradiation can be done in air, in vacuum, or in oxygen-free environment, including inert gases such as nitrogen or noble gases. Irradiation is done by using electron-beam, gamma irradiation, or x-ray irradiation.

The adverse oxidative effects of residual free radicals caused by ionizing radiation are reduced by diffusing an antioxidant such as α-tocopherol into high pressure crystallized, partially melted and cross-linked polyethylene. The antioxidant prevents oxidation of irradiated materials. Doping of polyethylene by an antioxidant is performed as described herein.

The adverse oxidative effects of residual free radicals caused by ionizing radiation is reduced by using a blend of polymer and additive, which is also an antioxidant, such as α-tocopherol to high pressure crystallize and irradiate.

In another aspect, the residual free radicals caused by ionizing radiation are removed by mechanical annealing, where the polyethylene is heated to a temperature below the melting point (less than about 150° C.), preferably 145° C., more preferably at about 140° C. and deformed mechanically to provide mobility for the residual free radicals to recombine and stabilize.

In another aspect, the residual free radicals generated during ionizing radiation is removed by heating polyethylene to melt. Melting of the irradiated polyethylene is used as part of high-pressure crystallization subsequent to irradiation.

A high crystalline polyethylene is made by a process comprising high-pressure crystallization of unirradiated polyethylene, followed by irradiation, and elimination of the free radicals generated during the process, with minimum compromise in the crystallinity achieved.

According to one aspect of the invention, polyethylene is pressurized to above about 10-1000 MPa (for example, at least about 150 MPa, 200 MPa, 250 MPa, 300 MPa, 310 MPa, 320 MPa, 380 MPa, 400 MPa, or 450 MPa), preferably at least about 150 MPa, more preferably at least 250 MPa, yet more preferably to above 320 MPa, heated to either about 180 or about 225° C., held at that temperature and that pressure, cooled to room temperature, reduced pressure to ambient, and irradiated at room temperature. Subsequently, one of the following processes can be employed in order to improve oxidation resistance of the high pressure crystallized polyethylene: a) doping the high pressure crystallized polyethylene with an antioxidant, such as vitamin E; or b) mechanically deforming the high pressure crystallized polyethylene below its melting point followed by annealing near its melting point, essentially applying any of the CIMA methods, and c) heating to above the melting point, pressurizing to at least about 10-1000 MPa (for example, at least about 150 MPa, 200 MPa, 250 MPa, 300 MPa, 310 MPa, 320 MPa, 380 MPa, 400 MPa, or 450 MPa), preferably at least about 150 MPa, more preferably at least 250 MPa, yet more preferably above 380 MPa, holding at this temperature and pressure, cooling to about room temperature, reducing pressure to ambient.

A potential draw-back of irradiating a highly crystalline polyethylene at room temperature can be that the reduced concentration of amorphous phase, where cross-linking primarily takes place, in a polyethylene with increased crystallinity can also reduce the concentration of crosslinks formed by irradiation. Therefore, it is preferable to irradiate polyethylene at an elevated temperature where the polymer is approximately 60% or less crystalline to increase the amorphous content. High pressure crystallized polyethylene exhibits two melting peaks, one at about 137° C. and the other at above about 140° C. The second peak is formed during high-pressure crystallization and represents extended chain crystals (larger ones). The following sequence of events is applied according to one aspect of the invention: Heated to a temperature below 140° C. to melt some of the smaller crystals and also cross-linked the regions that contain smaller crystals; irradiated at this temperature (warm irradiation (WI)), then one of the following processes are employed in order to improve oxidation resistance of the high pressure crystallized polyethylene:

a) doping the high-pressure crystallized polyethylene with an antioxidant, such as vitamin E; and b) melt by heating to above the melting point, then pressurizing to at least about 10-1000 MPa (for example, at least about 150 MPa, 200 MPa, 250 MPa, 300 MPa, 310 MPa, 320 MPa, 380 MPa, 400 MPa, or 450 MPa), preferably at least about 150 MPa, more preferably at least 250 MPa, yet more preferably above 320 MPa, holding pressure and temperature about constant, cooling to about room temperature, and reducing pressure to ambient. The melting step of this process will eliminate the crystals; therefore, the process is followed by high-pressure crystallization to achieve a high level of crystallinity.

In one aspect of the invention, the doping of high pressure crystallized polyethylene is carried out by diffusion of an additive, for example, α-tocopherol, such as vitamin E. According to one aspect of the invention, diffusion of the additive is accelerated by increasing the temperature and/or pressure.

According to another aspect of the invention, an additive is delivered in various forms, including in a pure form, for example, as pure vitamin E, or dissolved in a solvent.

According to another aspect of the invention, the diffusion rate of an additive into the polyethylene is increased by increasing the concentration of the additive solution, for example, a vitamin E solution.

In accordance with another aspect of the invention, diffusion rate of an antioxidant into the polyethylene is increased by swelling the high pressure crystallized polyethylene in a supercritical fluid, for example, in a supercritical $CO_2$, i.e., the temperature being above the supercritical temperature, which is 31.3° C., and the pressure being above the supercritical pressure, which is 73.8 bar.

Doping in the consolidated state also allows one to achieve a gradient of antioxidant in consolidated polymeric material. One can dope a certain thickness surface layer where the oxidation of the polymeric material in a medical device is of concern in terms of wear. This can be achieved by simply dipping or soaking finished devices, for example, a finished medical implant, for example, in pure vitamin E or in a solution of vitamin E at a given temperature and for a given amount of time.

According to the methods described herein, an antioxidant, for example, vitamin E, is doped into the high-pressure crystallized polymeric material before, during, or after irradiation.

It may be possible that the doped antioxidant can leach out of the polymeric material used in fabrication of medical implants or medical devices either during storage prior to use or during in vivo service. For a permanent medical device, the in vivo duration can be as long as the remaining life of the patient, which is the length of time between implantation of the device and the death of the patient, for example, 1-120 years. If leaching out of the antioxidant is an issue, the irradiation of the medical implant or medical device or irradiation of any portion thereof. CaO be carried out after doping the antioxidant. This can ensure cross-linking of the antioxidant to the host polymer through covalent bonds and thereby minimize or prevent loss of antioxidant from the medical implant or the device.

According to another aspect of the invention, antioxidant-doped polymeric material or an antioxidant-doped medical implant can be washed in an industrial washer with detergent before packaging and sterilization. An industrial washer, for example, a washer/dryer such as a HAMO T-21 or a washer/disinfectant/dryer such as a HAMO M-100 (HAMO AG, Pieterlen, Switzerland) can be used.

According to another aspect of the invention, antioxidant-doped polymeric material; or an antioxidant-doped medical implant is soaked in a solvent such as ethanol before packaging and sterilization. A solvent, in which the antioxidant dissolves, is chosen so that the cleaning environment can provide a conducive environment for removing the antioxidant from the polymeric material. This decreases the possibility of antioxidant leaching from the antioxidant-doped polymeric material. The solvent can be at room temperature or at elevated temperatures, under ambient pressure or under elevated pressures, still or stirred. The time for the antioxidant-doped polymeric material or medical implant in contact with the solvent can range from about an hour to at least as long as the time that the doping was done, preferably less than 16 hours.

According to another aspect of the invention, polymeric material, for example, resin powder, flakes, particles, or a mixture thereof, is mixed with an additive and then the mixture is consolidated. The consolidated additive-doped polymeric material (blend) is machined to use as a component in a medical implant or as a medical device.

According to another aspect of the invention, high-pressure crystallized polymeric material, for example, high pressure crystallized resin powder, molded Sheet, blown films, tubes, balloons, flakes, particles, or a mixture thereof, is doped with an additive, for example, vitamin E in the form of α-Tocopherol, by diffusion. High pressure crystallized polymeric material, for example, high pressure crystallized UHMWPE is soaked in 100% vitamin E or in a solution of α-Tocopherol in an alcohol, for example, ethanol or isopropanol. A solution of α-Tocopherol, about 50% by weight in ethanol is used to diffuse in to UHMWPE in contact with a supercritical fluid, such as $CO_2$.

The invention also relates to the following processing steps to fabricate medical devices made out of highly cross-linked polyethylene and containing metallic pieces such as bipolar hip replacements, tibial knee inserts with reinforcing metallic and polyethylene posts, intervertebral disc systems, and for any implant that contains a surface that cannot be readily sterilized by a gas sterilization method.

According to one aspect of the invention, the high pressure crystallized polyethylene component of a medical implant is in close contact with another material (that is a non-modular implant), such as a metallic mesh or back, a non-metallic mesh or back, a tibial tray, a patella tray, or an acetabular shell, wherein the polyethylene, such as resin powder, flakes and particles are directly compression molded to these counter faces. For example, a polyethylene tibial insert is manufactured by compression molding of polyethylene resin powder to a tibial tray, to a metallic mesh or back or to a non-metallic mesh or back. In the latter case, the mesh is shaped to serve as a fixation interface with the bone, through either bony ingrowth or the use of an adhesive, such as polymethylmethacrylate (PMMA) bone cement. These shapes are of various forms including, acetabular liner, tibial tray for total or unicompartmental knee implants, patella tray, and glenoid component, ankle, elbow or finger component. Another aspect of the invention relates to mechanical interlocking of the molded polyethylene with the other piece(s), for example, a metallic or a non-metallic piece, that makes up part of the implant. The consolidated polyethylene with metallic piece is then high-pressure crystallized (HPC) to achieve a highly crystalline polyethylene. The HPC can is carried out by either first heating or pressurizing the non-modular implant.

The interface geometry is crucial in that polyethylene assumes the geometry as its consolidated shape. Polyethylene has a remarkable property of 'shape memory' due to its very high molecular weight that results in a high density of physical entanglements. Following consolidation, plastic deformation introduces a permanent shape change, which attains a preferred high entropy shape when melted. This recovery of the original consolidated shape is due to the 'shape memory', which is achieved when the polyethylene is consolidated. Because of this shape memory, the mechanical interlock will remain intact during and after the high-pressure crystallization of the non-modular implant.

Another aspect of the invention provides that following the high-pressure crystallization of the polyethylene that was molded to the counterface with the mechanical interlock, the hybrid component is irradiated using ionizing radiation to a desired dose level, for example, about 25 kGy to about 1000 kGy, preferably between about 50 kGy and about 150 kGy. Another aspect of the invention discloses that the irradiation step generates residual free radicals and therefore, a melting step is introduced thereafter to quench the residual free radicals followed by another step of high-pressure crystallization. Since the polyethylene is first consolidated into the shape of the interface, thereby setting a 'shape memory' of the polymer, the polyethylene does not separate from the counterface during melting and subsequent high-pressure crystallization step.

In another aspect of the invention, there are provided methods of cross-linking polyethylene, to create a polyethylene-based medical device, wherein the device is immersed in an oxidation-resistant medium such as inert gas or inert fluid, wherein the medium is heated to above the melting point of the irradiated highly crystalline polyethylene, for example, high pressure crystallized UHMWPE (above about 140° C.) to eliminate the crystalline matter and to allow the recombination/elimination of the residual free radicals. Because the shape memory of the compression molded polymer is set at the mechanically interlocked interface and that memory is strengthened by the cross-linking step, there is no significant separation at the interface between the polyethylene and the counterface.

Another aspect of the invention provides that following the above steps of free radical elimination, the interface between the metal and the polymer become sterile due to the high irradiation dose level used during irradiation. When there is substantial oxidation on the outside surface of the HPC-polyethylene induced during the free radical elimination step or irradiation step, the device surface is further machined to remove the oxidized surface layer. In another aspect, the invention provides that in the case of a post-melting machining of an implant, the melting step is carried out in the presence of an inert gas.

Another aspect of the invention includes methods of sterilization of the fabricated device, wherein the device is further sterilized with ethylene oxide, gas plasma, or the other gases, when the interface is sterile but the rest of the component is not.

Heating and Pressurization Via the Melt Phase:

The hexagonal phase of polyethylene is achieved by going through the melt phase or by going through the orthorhombic phase (see FIG. 1A). The first is achieved by using heating and pressurization methods such that immediately before the hexagonal phase transition is encountered, the sample is in the melt phase.

Figure 1B:
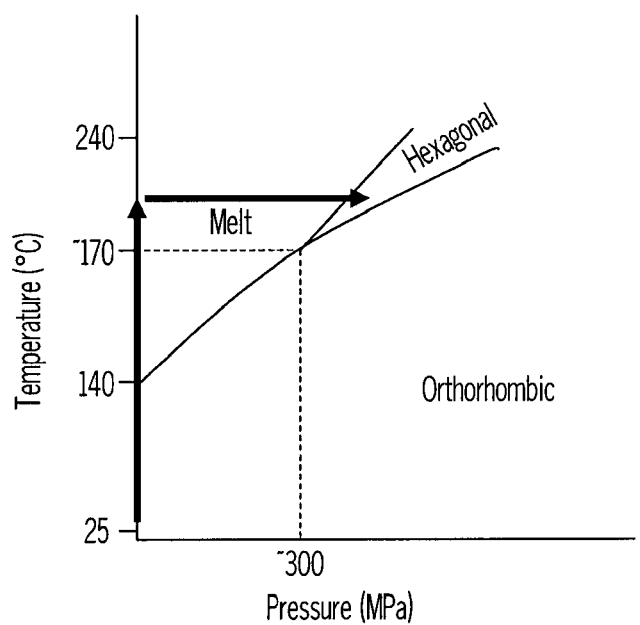
FIG. 1B shows a heating and pressurization scheme where the sample is first heated to above the melting temperature at ambient pressure to the high pressure crystallization temperature and pressurized to transition to the hexagonal phase from the melt phase.

In one embodiment, the sample is first heated to a temperature above the melting temperature of polyethylene under an ambient pressure (about 135° C.) or to above the melting temperature of polyethylene at about 40,000 psi, subsequently pressurized so that the melt to hexagonal phase transition is achieved. An example of the heating and pressurization cycle for this embodiment is shown in FIG. 1B.

Figure 1C:
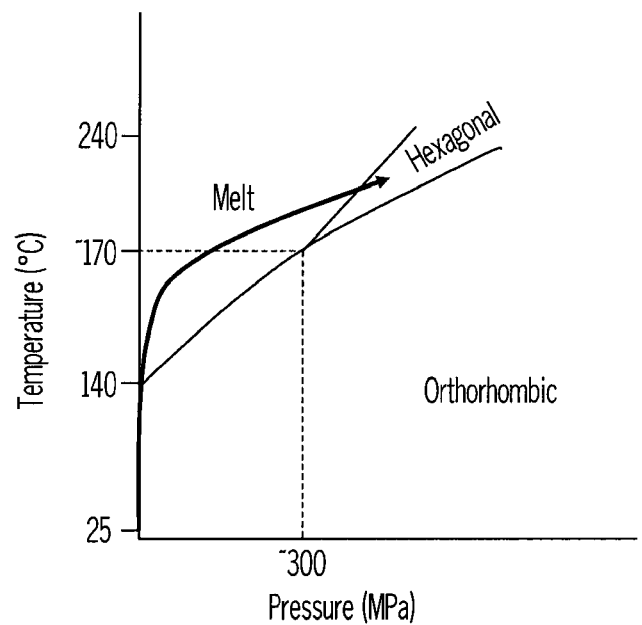
FIG. 1C shows a heating and pressurization scheme where the sample heated to above the melting temperature to the high pressure crystallization temperature and concurrently pressurized to transition to the hexagonal phase from the melt phase.

In another embodiment, the sample is heated and pressurized at the same time so that first the transition from the orthorhombic phase into the melt phase is achieved, then the transition from the melt phase into the hexagonal phase is achieved (see FIG. 1C, for example).

Figure 1D:
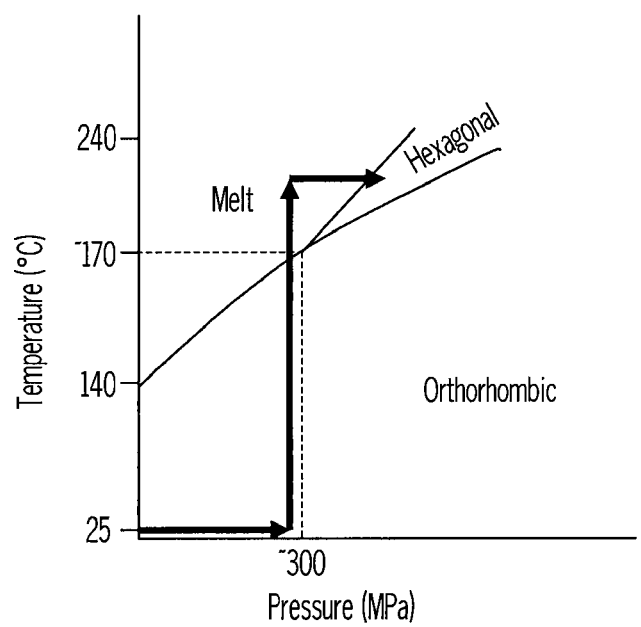
FIG. 1D shows a heating and pressurization scheme where the sample is pressurized to slightly below the triple point pressure, then heated to above the melt, then pressurized further to transition to the hexagonal phase from the melt phase.

In another embodiment, the sample is pressurized first to a pressure below the triple point of the polymer, subsequently heated such that the melt phase transition is achieved at this pressure, subsequently further pressurized to achieve the melt to hexagonal phase transition (see FIG. 1D, for example).

Figure 1E:
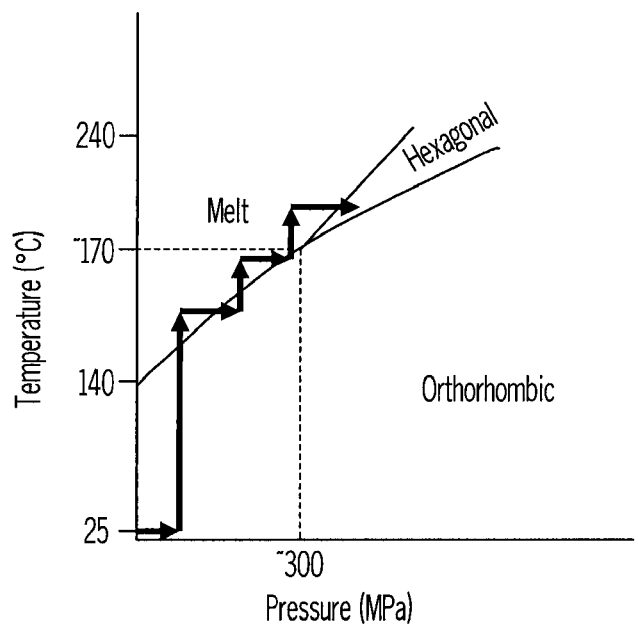
FIG. 1E shows a heating and pressurization scheme where the sample is pressurized and heated in subsequent steps transitioning in and out of the melt and orthorhombic phases until the triple point pressure and temperature, then it is heated and pressurized to transition to the hexagonal phase from the melt phase.

In another embodiment, the sample is heated and pressurized in a stepwise manner in the orthorhombic or melt phases as long as the transition to the hexagonal phase is achieved from the melt phase (see FIG. 1E, for example).

Figure 1F:
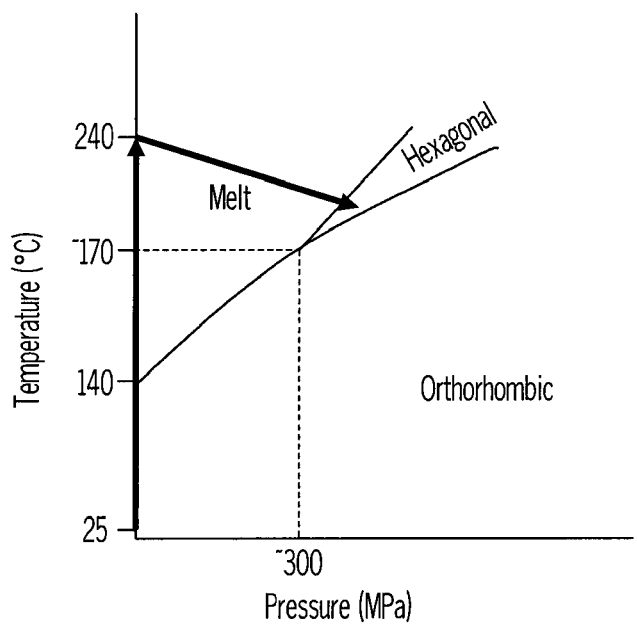
FIG. 1F shows a heating and pressurization scheme where the sample is heated to above the desired high pressure crystallization temperature and subsequently cooled and pressurized at the same time to transition into the hexagonal phase from the melt phase.

In another embodiment, the sample is heated above the desired high pressure crystallization temperature, then subsequently cooled while pressurizing such that the transition to the hexagonal phase is achieved from the melt phase (see FIG. 1F, for example).

Figure 1G:
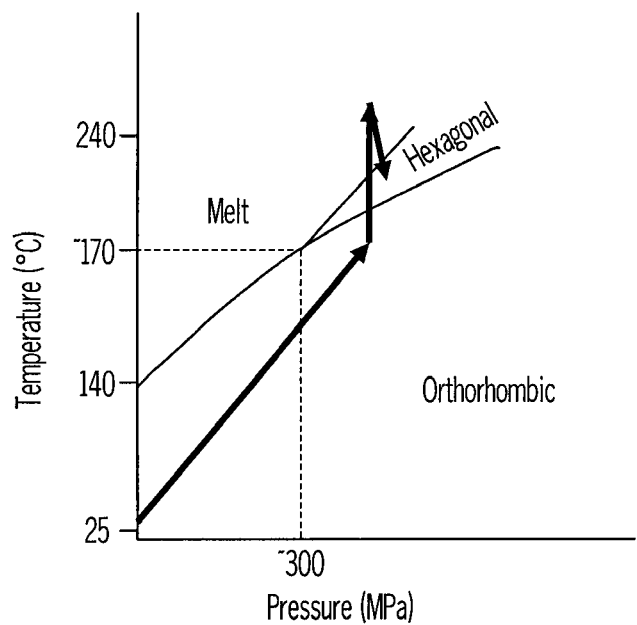
FIG. 1G shows a heating and pressurization scheme where the sample is heated and pressurized at the same time to about the desired high pressure crystallization pressure, then heated such that the sample is melted at this pressure and then cooled and further pressurized if desired to transition into the hexagonal phase from the melt phase.

In another embodiment, heating and pressurization is carried out such that the sample is heated and pressurized through the hexagonal phase into the melt phase, then is subsequently cooled and depressurized to crystallize in the hexagonal phase (see FIG. 1G, for example).

Figure 1H:
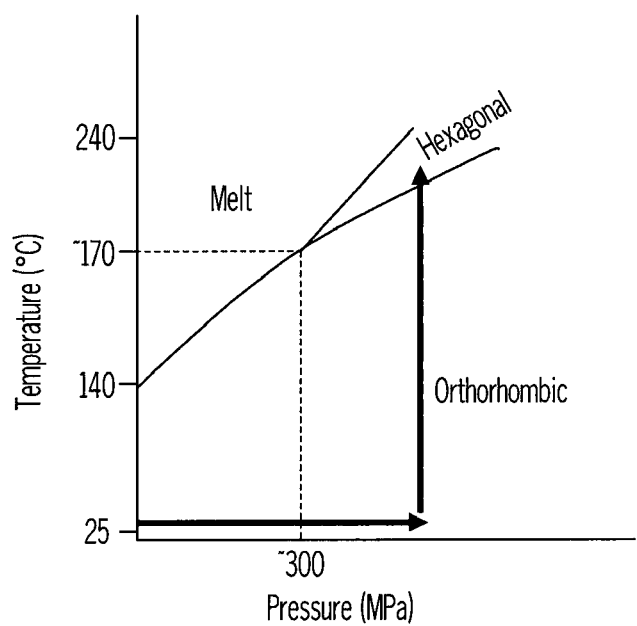
FIG. 1H shows a heating and pressurization scheme where the sample is pressurized to about the desired high pressure annealing pressure and heated to transition to the hexagonal phase from the orthorhombic phase.

Heating and Pressurization Via the Orthorhombic Phase:

Alternatively, to enter the hexagonal phase from the melt phase, the sample is crystallized in the hexagonal phase by going through the orthorhombic phase (see FIG. 1A, for example). In one embodiment, the sample is pressurized to above the triple point, and subsequently heated to achieve the orthorhombic to hexagonal phase transition (see FIG. 1H, for example).

Figure 1I:
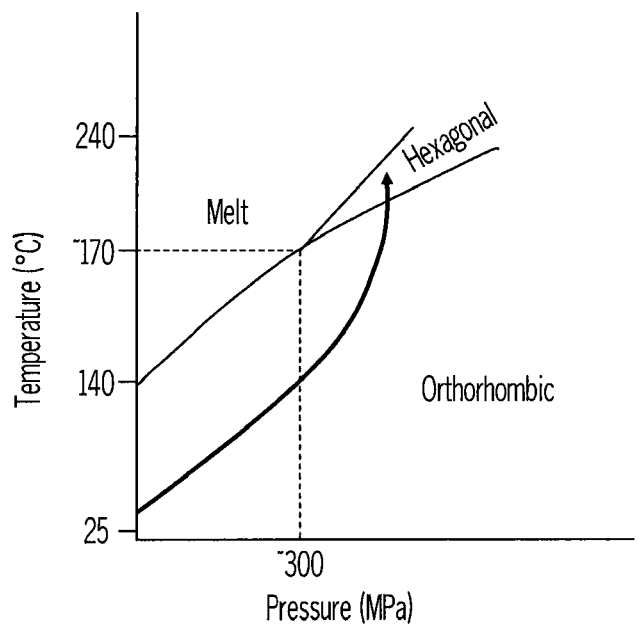
FIG. 1I shows a heating and pressurization scheme where the sample is concurrently heated and pressurized to transition to the hexagonal phase from the orthorhombic phase.
Figure 1J:
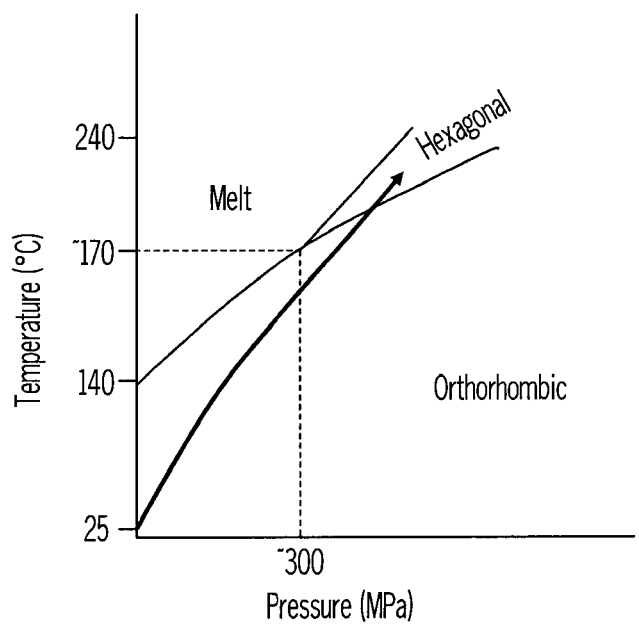
FIG. 1J shows a heating and pressurization scheme where the sample is concurrently heated and pressurized to transition to the hexagonal phase from the orthorhombic phase.

In another embodiment, pressurization and heating is done at the same time without encountering the melt phase and such that the hexagonal phase transition is achieved from the orthorhombic phase (see FIGS. 1I and 1J, for example).

Figure 1K:
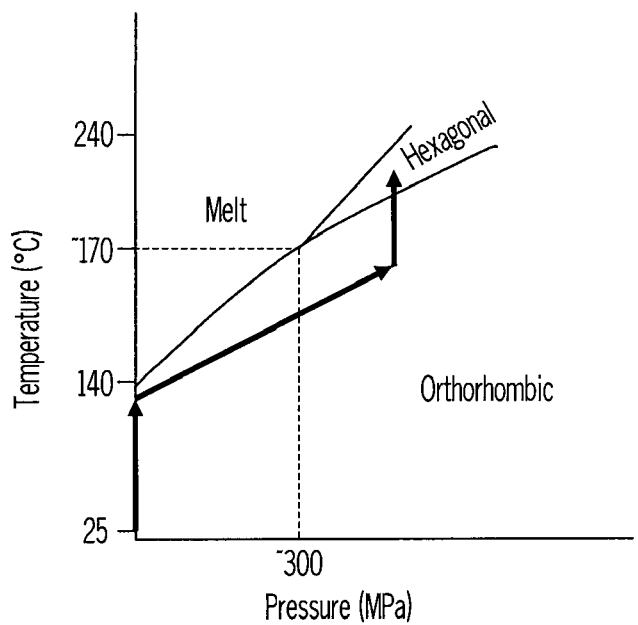
FIG. 1K shows a heating and pressurization scheme where the sample is heated to below the melt at ambient pressure, then concurrently heated and pressurized to the desired high pressure annealing pressure and below the phase transition temperatures at this pressure, then it is further heated to transition to the hexagonal phase from the orthorhombic phase.

In another embodiment, the sample is first heated to a temperature below the melting temperature of the polymer at ambient pressure, subsequently heated and pressurized without encountering the melt phase such that the hexagonal phase transition is achieved from the orthorhombic phase (see FIG. 1K, for example).

Figure 1L:
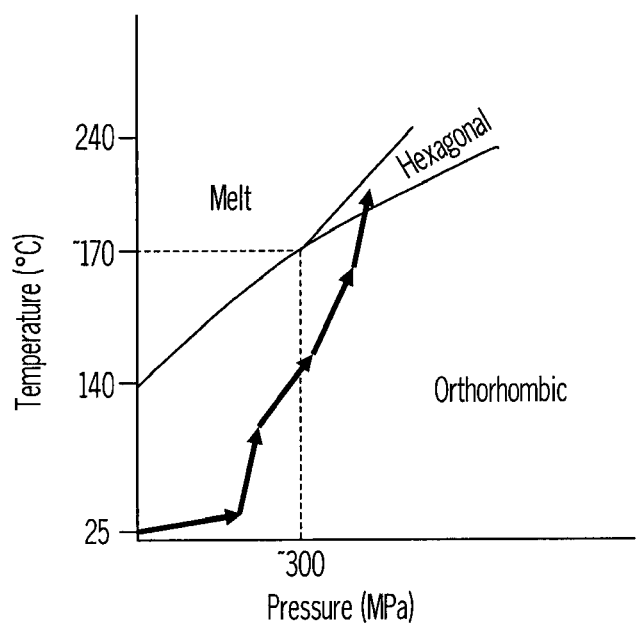
FIG. 1L shows a heating and pressurization scheme where the sample is heated and pressurized in subsequent steps to transition to the hexagonal phase from the orthorhombic phase.

In another embodiment, heating and pressurization from the orthorhombic phase at ambient pressure and temperature is done stepwise at different rates to achieve the orthorhombic to hexagonal phase transition (see FIG. 1L, for example).

Figure 1M:
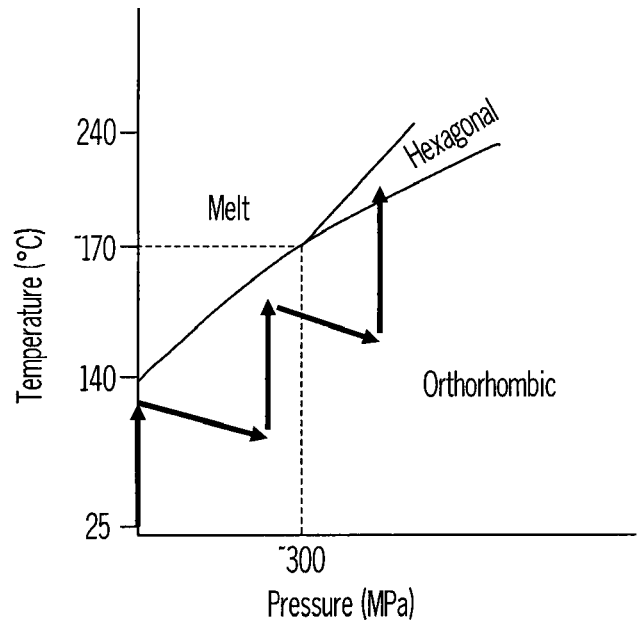
FIG. 1M shows a heating and pressurization scheme where the sample is heated and pressurized in subsequent steps comprising heating and concurrent cooling and pressurization to transition to the hexagonal phase from the orthorhombic phase.

In another embodiment, the sample is first heated to a temperature below the melting point of the polymer at ambient pressure, cooled while pressurizing, heated further, and this process can be repeated until the orthorhombic to hexagonal phase transition is achieved (see FIG. 1M, for example).

Figure 1N:
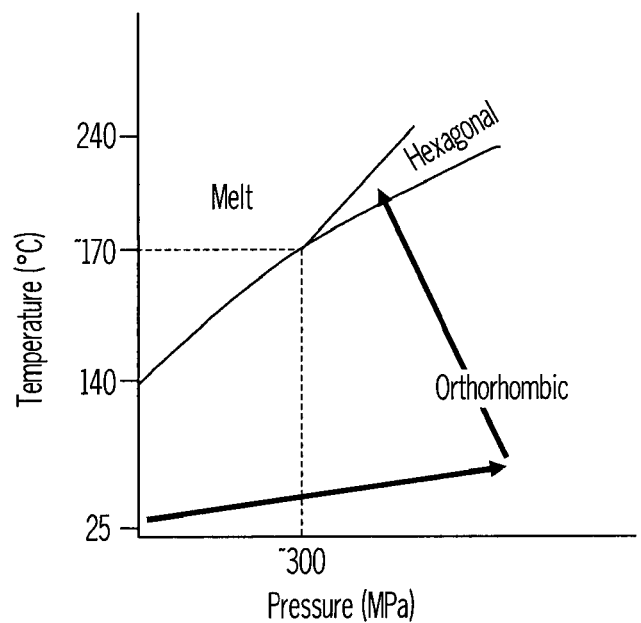
FIG. 1N shows a heating and pressurization scheme where the sample is heated and pressurized to a pressure above the desired high pressure annealing pressure in the orthorhombic phase, then heated and depressurized to transition to the hexagonal phase from the orthorhombic phase.

In yet another embodiment, the sample is first pressurized to a pressure above the desired high pressure crystallization pressure in the orthorhombic phase, then subsequently depressurized while heating to achieve the orthorhombic to hexagonal phase transition (see FIG. 1N, for example).

Cooling and Depressurization:

Once the hexagonal phase transition has been achieved and the polymer has stayed in the hexagonal phase for a desired period of time, then cooling and depressurization is achieved in different ways. In order to preserve the crystals formed in the hexagonal phase, the sample has to be cooled down in a way that the melt transition is not fully encountered. The following embodiments describe several methods as examples to how this is achieved.

Figure 1O:
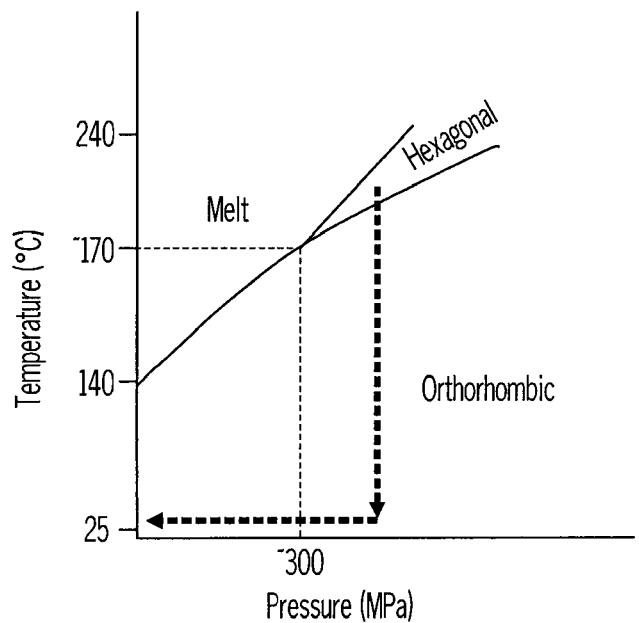
FIG. 1O shows a cooling and depressurization scheme where the sample is cooled to about room temperature at the high pressure crystallization or annealing pressure to transition from the hexagonal phase to the orthorhombic phase and the pressure is subsequently released in the orthorhombic phase.

In one embodiment, the sample is cooled down under constant pressure to about room temperature and subsequently the pressure is released. In this manner, first the hexagonal to orthorhombic phase transition is achieved and then the sample is depressurized in the orthorhombic phase (see FIG. 1O, for example). In this method, what is meant by constant pressure is pressure within about 5000 psi of the original value.

Figure 1P:
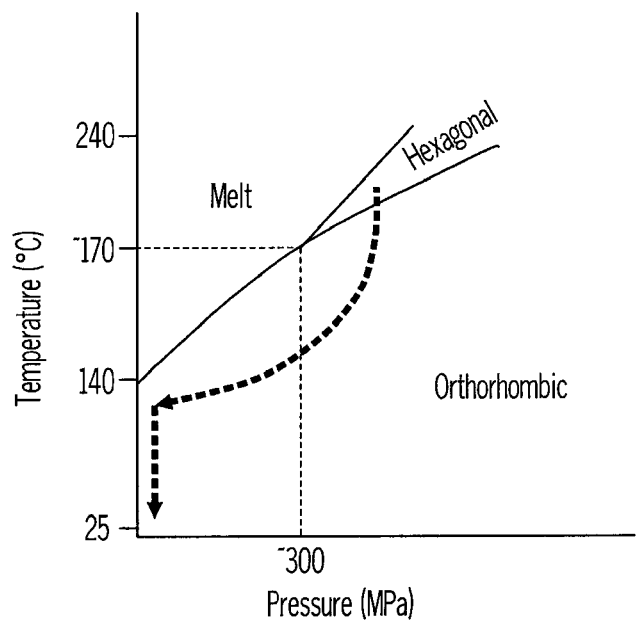
FIG. 1P shows a cooling and depressurization scheme where the sample is cooled to about below the melting temperature at ambient pressure and depressurized to transition from the hexagonal phase into the orthorhombic phase, then further cooled at ambient pressure to about room temperature in the orthorhombic phase.
Figure 1Q:
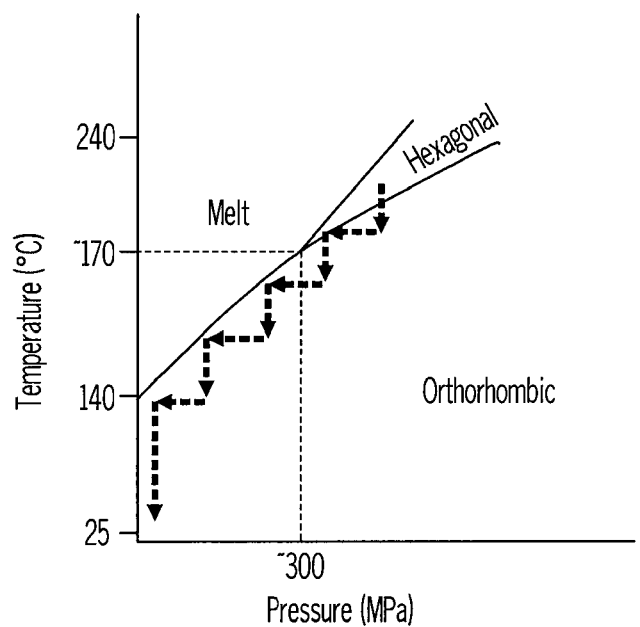
FIG. 1Q shows a cooling and depressurization scheme where the sample is cooled and depressurized in subsequent steps to transition from the hexagonal phase to the orthorhombic phase and eventually to ambient pressure and about room temperature in the orthorhombic phase.
Figure 1R:
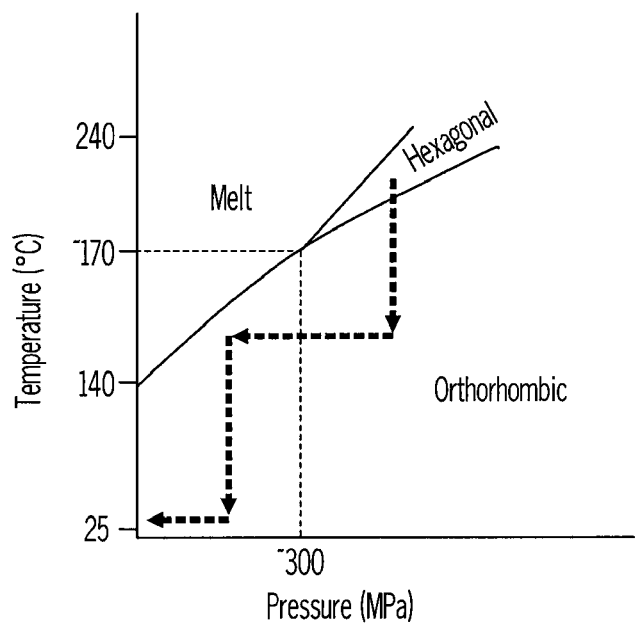
FIG. 1R shows a cooling and depressurization scheme where the sample is cooled at the high pressure crystallization or annealing pressure to transition from the hexagonal phase into the orthorhombic phase to a temperature above the melting point at ambient pressure, held at this temperature while depressurizing in the orthorhombic phase, then further cooled to about room temperature and depressurized to ambient pressure in the orthorhombic phase.
Figure 1S:
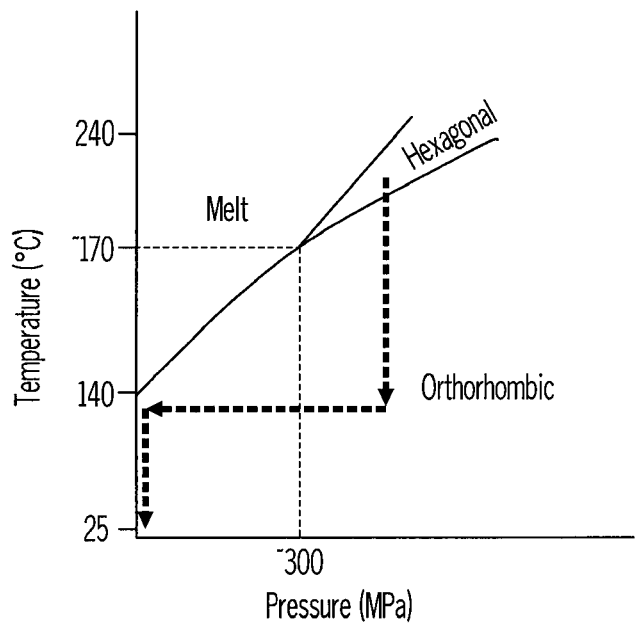
FIG. 1S shows a cooling and depressurization scheme where the sample is cooled at the high pressure crystallization or annealing pressure to transition from the hexagonal phase into the orthorhombic phase to a temperature below the melting point at ambient pressure, held at this temperature while depressurizing in the orthorhombic phase, then further cooled to about room temperature in the orthorhombic phase.

In another embodiment, the sample is cooled down and depressurized at the same time in a non-linear fashion without encountering the melt phase (see FIG. 1P, for example). The pressure is released at the same time cooling the sample down to below the melting temperature of the polymer at ambient pressure.

Alternatively, the sample is cooled and depressurized in a stepwise fashion without encountering the melt phase (see FIGS. 1Q-1U, for example). In one embodiment, the sample is cooled to and maintained at a temperature above the melting point of the polymer at ambient pressure while depressurizing partially (see FIG. 1R, for example) or cooled to and maintained at a temperature below the melting point of the polymer at ambient pressure while depressurizing partially (see FIG. 1S, for example). Subsequently, the sample is further cooled to about room temperature and the rest of the pressure is released.

Figure 1T:
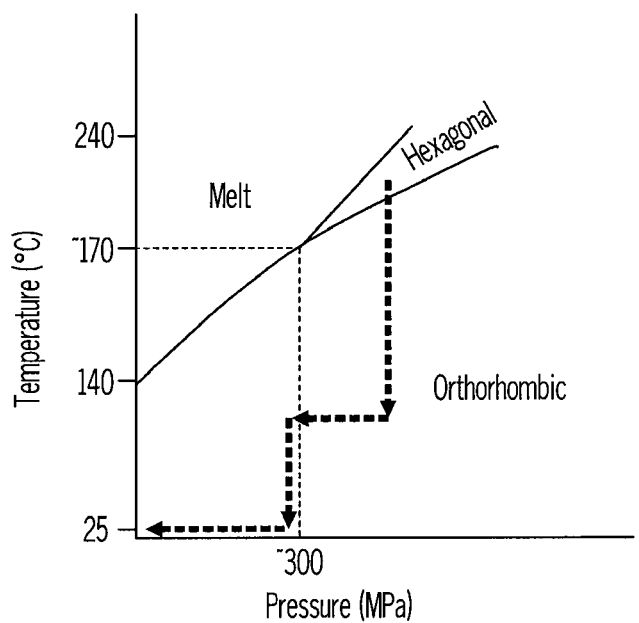
FIG. 1T shows a cooling and depressurization scheme where the sample is cooled at the high pressure crystallization or annealing pressure to transition from the hexagonal phase into the orthorhombic phase to a temperature about the melting point at ambient pressure, held at this temperature while depressurizing in the orthorhombic phase to about the triple point pressure, then further cooled to about room temperature and depressurized to about ambient pressure in the orthorhombic phase.

In another embodiment, the polymer sample is cooled down under constant pressure to about a temperature below the melting point of the polymer at ambient pressure and subsequently the pressure is released (see FIG. 1T, for example). In this manner, first the hexagonal to orthorhombic phase transition is achieved and then the sample is depressurized in the orthorhombic phase. In this method, what is meant by constant pressure is pressure within about 5000 psi of the original value.

According to one aspect of the invention, the cooling rate is 0.001° C./min to 500° C./min, more preferably about 0.1° C.min to 5° C./min, more preferably about 1° C./min. In another aspect of the invention, the depressurization is about 100 psi/min to 500,000 psi/min, more preferably about 1000 psi/min to 45000 psi/min, more preferably about 10,000 psi/min. In another aspect of the invention, the holding time at any of the constant pressure or temperature steps is from 0.1 minute to 500 hours, more preferably about 1 minute to 600 minutes, more preferably about 1 hour to 8 hours, more preferably about 4 hours. The effect of holding time on the sample depends on the sample size. If the entire sample does not come to same temperature, there can be gradients in the polymer. Gradients are desirable for certain applications.

Figure 1U:
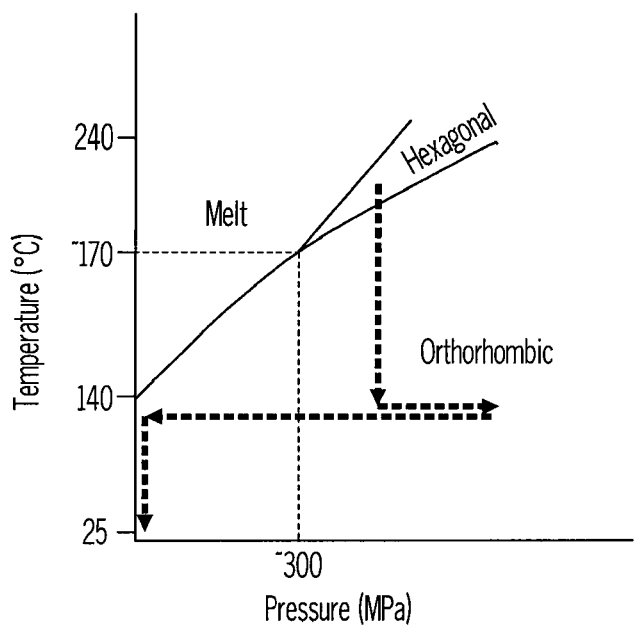
FIG. 1U shows a cooling and depressurization scheme where the sample is cooled at the high pressure crystallization or annealing pressure to transition from the hexagonal phase into the orthorhombic phase to a temperature about the melting point at ambient pressure, pressurized at this temperature in the orthorhombic phase, then depressurized to about ambient pressure and then further cooled to about room temperature in the orthorhombic phase.

Alternatively, in another aspect of the invention, the sample is cooled down to below the melting temperature of the polymer at ambient pressure, then pressurized further, maintained at this pressure and temperature, then the pressure is released, then the sample is cooled down to about room temperature (See FIG. 1U, for example).

Figure 1V:
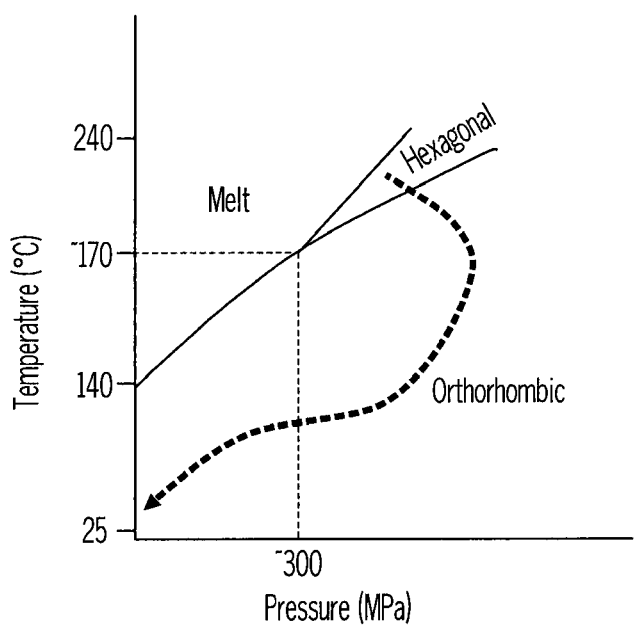
FIG. 1V shows a cooling and depressurization scheme where the sample is cooled to transition from the hexagonal phase into the orthorhombic phase and eventually to ambient pressure and temperature comprising pressurization in the orthorhombic phase.
Figure 1W:
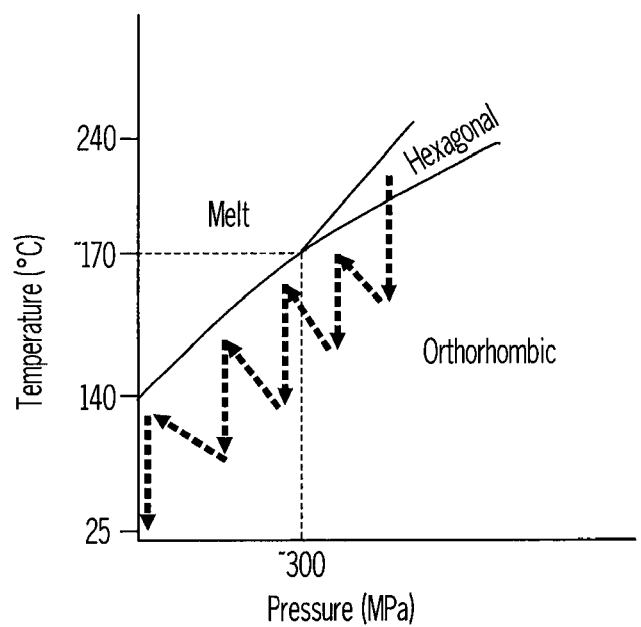
FIG. 1W shows a cooling and depressurization scheme where the sample is cooled, then concurrently heated and depressurized in a stepwise manner to transition from the hexagonal phase into the orthorhombic phase and eventually to ambient pressure and temperature in the orthorhombic phase.

In one embodiment, the sample is cooled down and depressurized overall via cooling, heating and depressurization and pressurization steps (See FIGS. 1V and 1W, for example).

In another embodiment, the sample is taken into the melt transition while cooling and depressurization. Depending on the time spent in the melt phase and the sample size, part or all of the extended chain crystals formed in the hexagonal phase is melted and if the sample is subsequently immediately cooled down and depressurized to about room temperature and ambient pressure, the melted crystals are recrystallized as folded chain crystals.

Irradiation of a Finished Product Made of a Blend of UHMWPE with an Additive Followed by High-Pressure Crystallization:

According to one aspect of the invention, a finished product, for example, an article, a medical device, or a medical prosthesis and the like, is irradiated and then high pressure crystallized as follows: Polymeric material, for example, resin powder, flakes, particles, or a mixture thereof, is mixed/blended with an additive, for example, an antioxidant, preferably vitamin E (preferably less than about 10%, more preferably less than 5%, more preferably less than 0.3%, and yet more preferably 0.1% vitamin E) and then form an article or a medial device by:

a. Consolidating the blend, preferably by adding a step to anneal the consolidated blend to remove thermal stresses; and
  b. Machining the blend to form a finished product; or
  c. Direct compression molding the blend to form a finished product.

The finished product is irradiated to at least 1 kGy, preferably about 25 kGy to about 1000 kGy or more, more preferably a dose of about 25, 50, 75, 100, 125, 150, 175, or 200 kGy by gamma, e-beam, or x-ray.

The irradiated finished product is high pressure crystallized by either:
  a. Heating to a temperature above the melting point of the irradiated polyethylene under an ambient pressure, pressurizing to at least about 10-1000 MPa (for example, at least about 150 MPa, 200 MPa, 250 MPa, 300 MPa, 310 MPa, 320 MPa, 380 MPa, 400 MPa, or 450 MPa), preferably at least about 150 MPa, more preferably at least about 250 MPa, cooling to about room temperature while under pressure, and releasing the pressure; or
  b. Pressurizing to at least about 10-1000 MPa (for example, at least about 150 MPa, 200 MPa, 250 MPa, 300 MPa, 310 MPa, 320 MPa, 380 MPa, 400 MPa, or 450 MPa), preferably at least about 150 MPa, more preferably at least about 250 MPa, heating to a temperature above the melting point of the irradiated polyethylene under an ambient pressure, cooling to about room temperature, and releasing pressure.

The high pressure crystallized finished product can be packaged and sterilized.

Irradiation, Melting, and Machining of a Finished Product Prior to High-Pressure Crystallization:

According to another aspect of the invention, a finished product, for example, an article, a medical device or a medical prosthesis and the like, is irradiated, melted, machined, and then high pressure crystallized as follows:

Polymeric material is irradiated, melted, and machined to form a finished product, for example, an article, a medical device, or a medical prosthesis and the like.

The finished product is high pressure crystallized by either:
  a. Heating to a temperature above the melting point of the irradiated polyethylene under an ambient pressure, pressurizing to at least about 10-1000 MPa (for example, at least about 150 MPa, 200 MPa, 250 MPa, 300 MPa, 310 MPa, 320 MPa, 380 MPa, 400 MPa, or 450 MPa), preferably at least about 150 MPa, more preferably at least about 250 MPa, cooling to about room temperature while under pressure, and releasing the pressure; or
  b. Pressurizing to at least about 10-1000 MPa (for example, at least about 150 MPa, 200 MPa, 250 MPa, 300 MPa, 310 MPa, 320 MPa, 380 MPa, 400 MPa, or 450 MPa), preferably at least about 150 MPa, more preferably at least about 250 MPa, heating to a temperature above the melting point of the irradiated polyethylene under an ambient pressure, cooling to about room temperature, and releasing pressure.

The high pressure crystallized finished product can be packaged and sterilized.

Irradiation and Machining of a Finished Product Prior to High-Pressure Crystallization:

According to another aspect of the invention, a finished product, for example, an article, a medical device or a medical prosthesis and the like, is irradiated, machined, and then high pressure crystallized as follows:

Polymeric material is irradiated and machined to form a finished product, for example, an article, a medical device, or a medical prosthesis and the like.

The finished product is high pressure crystallized by either:
  a. Heating to a temperature above the melting point of the irradiated polyethylene under an ambient pressure, pressurizing to at least about 10-1000 MPa (for example, at least about 150 MPa, 200 MPa, 250 MPa, 300 MPa, 310 MPa, 320 MPa, 380 MPa, 400 MPa, or 450 MPa), preferably at least about 150 MPa, more preferably at least about 250 MPa, cooling to about room temperature while under pressure, and releasing the pressure; or
  b. Pressurizing to at least about 10-1000 MPa (for example, at least about 150 MPa, 200 MPa, 250 MPa, 300 MPa, 310 MPa, 320 MPa, 380 MPa, 400 MPa, or 450 MPa), preferably at least about 150 MPa, more preferably at least about 250 MPa, heating to a temperature above the melting point of the irradiated polyethylene under an ambient pressure, cooling to about room temperature, and releasing pressure.

The high pressure crystallized finished product can be packaged and sterilized.

Warm Irradiation, Melting, and Machining of a Finished Product Prior to High-Pressure Crystallization:

According to another aspect of the invention, a finished product, for example, an article, a medical device or a medical prosthesis and the like, is warm irradiated, melted, machined, and then high pressure crystallized as follows:

Polymeric material is warm irradiated to above room temperature, such as a temperature above about 80° C. and below the melting point of the polymeric material. The warm irradiated polymeric material is melted, and machined to form a finished product, for example, an article, a medical device, or a medical prosthesis and the like.

The finished product is high pressure crystallized by either:
  a. Heating to a temperature above the melting point of the irradiated polyethylene under an ambient pressure, pressurizing to at least about 10-1000 MPa (for example, at least about 150 MPa, 200 MPa, 250 MPa, 300 MPa, 310 MPa, 320 MPa, 380 MPa, 400 MPa, or 450 MPa), preferably at least about 150 MPa, more preferably at least about 250 MPa, cooling to about room temperature while under pressure, and releasing the pressure; or
  b. Pressurizing to at least about 10-1000 MPa (for example, at least about 150 MPa, 200 MPa, 250 MPa, 300 MPa, 310 MPa, 320 MPa, 380 MPa, 400 MPa, or 450 MPa), preferably at least about 150 MPa, more preferably at least about 250 MPa, heating to a temperature above the melting point of the irradiated polyethylene under an ambient pressure, cooling to about room temperature, and releasing pressure.

The high pressure crystallized finished product can be packaged and sterilized.

Warm Irradiation and Machining of a Finished Product Prior to High-Pressure Crystallization:

According to another aspect of the invention, a finished product, for example, an article, a medical device or a medical prosthesis and the like, is warm irradiated, machined, and then high pressure crystallized as follows:

Polymeric material is warm irradiated to above room temperature, such as a temperature above about 80° C. and below the melting point of the polymeric material and machined to form a finished product, for example, an article, a medical device, or a medical prosthesis and the like.

The finished product is high pressure crystallized by either:
  a. Heating to a temperature above the melting point of the irradiated polyethylene under an ambient pressure, pressurizing to at least about 10-1000 MPa (for example, at least about 150 MPa, 200 MPa, 250 MPa, 300 MPa, 310 MPa, 320 MPa, 380 MPa, 400 MPa, or 450 MPa), preferably at least about 150 MPa, more preferably at least about 250 MPa, cooling to about room temperature while under pressure, and releasing the pressure; or
  b. Pressurizing to at least about 10-1000 MPa (for example, at least about 150 MPa, 200 MPa, 250 MPa, 300 MPa, 310 MPa, 320 MPa, 380 MPa, 400 MPa, or 450 MPa), preferably at least about 150 MPa, more preferably at least about 250 MPa, heating to a temperature above the melting point of the irradiated polyethylene under an ambient pressure, cooling to about room temperature, and releasing pressure.

The high pressure crystallized finished product can be packaged and sterilized.

Cold Irradiation and Mechanically Annealing (CIMA) and Machining of a Finished Product Prior to High-Pressure Crystallization:

According to another aspect of the invention, a finished product, for example, an article, a medical device or a medical prosthesis and the like, is irradiated by a CIMA method, machined, and then high pressure crystallized as follows:

Polymeric material is irradiated and mechanically deformed at an elevated temperature, such as above 90° C. and below 140° C. and deformed under pressure until cooled down to room temperature, annealed above room temperature, such as at above 90° C. and below 140° C. to recover the deformed state, and machined to form a finished product, for example, an article, a medical device, or a medical prosthesis and the like.

The finished product is high pressure crystallized by either:
a. Heating to a temperature above the melting point of the irradiated polyethylene under an ambient pressure, pressurizing to at least about 10-1000 MPa (for example, at least about 150 MPa, 200 MPa, 250 MPa, 300 MPa, 310 MPa, 320 MPa, 380 MPa, 400 MPa, or 450 MPa), preferably at least about 150 MPa, more preferably at least about 250 MPa, cooling to about room temperature while under pressure, and releasing the pressure; or
b. Pressurizing to at least about 10-1000 MPa (for example, at least about 150 MPa, 200 MPa, 250 MPa, 300 MPa, 310 MPa, 320 MPa, 380 MPa, 400 MPa, or 450 MPa), preferably at least about 150 MPa, more preferably at least about 250 MPa, heating to a temperature above the melting point of the irradiated polyethylene under an ambient pressure, cooling to about room temperature, and releasing pressure.

The high pressure crystallized finished product can be packaged and sterilized.

DEFINITIONS

"High pressure crystallized" (HPC) refers to a state of a polymeric material that has undergone high-pressure crystallization process, according to the invention, as described herein.

"High-pressure crystallization" refers to a method of making high pressure crystallized polyethylene, according to the invention, as described herein.

The term "highly crystalline" or "high crystallinity" refers to a state of a material of at least about 51% crystallinity.

An "additive" refers to what is known in the art as additional component other than the polymeric material. An "additive" can be, for example, a nucleating agent, an antioxidant, a lipid, a low molecular weight polyethylene.

"Antioxidant" refers to what is known in the art as (see, for example, WO 01/80778. U.S. Pat. No. 6,448,315). Alpha- and delta-tocopherol; propyl, octyl, or dedocyl gallates; lactic, citric, and tartaric acids and their salts; orthophosphates, tocopherol acetate. Preferably vitamin E. An "additive" includes antioxidants and the like.

"Supercritical fluid" refers to what is known in the art, for example, supercritical propane, acetylene, carbon dioxide ($CO_2$). In this connection the critical temperature is that temperature above which a gas cannot be liquefied by pressure alone. The pressure under which a substance may exist as a gas in equilibrium with the liquid at the critical temperature is the critical pressure. Supercritical fluid condition generally means that the fluid is subjected to such a temperature and such a pressure that a supercritical fluid and thereby a supercritical fluid mixture is obtained, the temperature being above the supercritical temperature, which for $CO_2$ is 31.3° C., and the pressure being above the supercritical pressure, which for $CO_2$ is 73.8 bar. More specifically, supercritical condition refers to a condition of a mixture, for example, UHMWPE with an antioxidant, at an elevated temperature and pressure, when a supercritical fluid mixture is formed and then evaporate $CO_2$ from the mixture. UHMWPE doped with an antioxidant is obtained (see, for example, U.S. Pat. No. 6,448,315 and WO 02/26464)

The term "compression molding" as referred herein related generally to what is known in the art and specifically relates to high temperature molding polymeric material wherein polymeric material is in any physical state, including powder form, is compressed into a slab form or mold of a medical implant, for example, a tibial insert, an acetabular liner, a glenoid liner, a patella, or an unicompartmental insert.

The term "direct compression molding" as referred herein related generally to what is known in the art and specifically relates to molding applicable in polyethylene-based devices, for example, medical implants wherein polyethylene in any physical state, including powder form, is compressed to solid support, for example, a metallic back, metallic mesh, or metal surface containing grooves, undercuts, or cutouts. The compression molding also includes high temperature compression molding of polyethylene at various states, including resin powder, flakes and particles, to make a component of a medical implant, for example, a tibial insert, an acetabular liner, a glenoid liner, a patella, or an unicompartmental insert, to the counterface.

The term "mechanically interlocked" refers generally to interlocking of polyethylene and the counterface, that are produced by various methods, including compression molding, heat and irradiation, thereby forming an interlocking interface, resulting into a 'shape memory' of the interlocked polyethylene. Components of a device having such an interlocking interface can be referred to as a "hybrid material". Medical implants having such a hybrid material, contain a substantially sterile interface.

The term "substantially sterile" refers to a condition of an object, for example, an interface or a hybrid material or a medical implant containing interface(s), wherein the interface is sufficiently sterile to be medically acceptable, i.e., will not cause an infection or require revision surgery.

"Metallic mesh" refers to a porous metallic surface of various pore sizes, for example, 0.1-3 mm. The porous surface can be obtained through several different methods, for example, sintering of metallic powder with a binder that is subsequently removed to leave behind a porous surface; sintering of short metallic fibers of diameter 0.1-3 mm; or sintering of different size metallic meshes on top of each other to provide an open continuous pore structure.

"Bone cement" refers to what is known in the art as an adhesive used in bonding medical devices to bone. Typically, bone cement is made out of polymethylmethacrylate (PMMA).

"High temperature compression molding" refers to the compression molding of polyethylene in any form, for example, resin powder, flakes or particles, to impart new geometry under pressure and temperature. During the high temperature (above the melting point of polyethylene) compression molding, polyethylene is heated to above its melting point, pressurized into a mold of desired shape and allowed to cool down under pressure to maintain a desired shape.

"Shape memory" refers to what is known in the art as the property of polyethylene, for example, an UHMWPE, that attains a preferred high entropy shape when melted. The preferred high entropy shape is achieved when the resin powder is consolidated through compression molding.

The phrase "substantially no detectable residual free radicals" refers to a state of a polyethylene component, wherein enough free radicals are eliminated to avoid oxidative degradation, which can be evaluated by electron spin resonance (ESR). The phrase "detectable residual free radicals" refers to the lowest level of free radicals detectable by ESR. The lowest level of free radicals detectable with state-of-the-art instruments is about $10^{14}$ spins/gram and thus the term "detectable" refers to a detection limit of $10^{14}$ spins/gram by ESR.

The terms "about" or "approximately" in the context of numerical values and ranges refers to values or ranges that approximate or are close to the recited values or ranges such that the invention can perform as intended, such as having a desired degree of crystallinity or cross-linking and/or a desired lack of free radicals, as is apparent to the skilled person from the teachings contained herein. This is due, at least in part, to the varying properties of polymer compositions. Thus these terms encompass values beyond those resulting from systematic error.

Polymeric Material:

Ultra-high molecular weight polyethylene (UHMWPE) refers to linear non-branched chains of ethylene having molecular weights in excess of about 500,000, preferably above about 1,000,000, and more preferably above about 2,000,000. Often the molecular weights can reach about 8,000,000 or more. By initial average molecular weight is meant the average molecular weight of the UHMWPE starting material, prior to any irradiation. See U.S. Pat. No. 5,879,400, PCT/US99/16070, filed on Jul. 16, 1999, PCT/US97/02220, filed Feb. 11, 1997, and US Patent publication 20030149125 (U.S. application Ser. No. 10/252,582), filed Sep. 24, 2002.

The products and processes of this invention also apply to various types of polymeric materials, for example, any polyolefin, including high-density-polyethylene, low-density-polyethylene, linear-low-density-polyethylene, ultra-high molecular weight polyethylene (UHMWPE), or mixtures thereof. Polymeric materials, as used herein, also applies to polyethylene of various forms, for example, resin powder, flakes, particles, powder, or a mixture thereof, or a consolidated form derived from any of the above.

The term "additive" refers to any material that can be added to a base polymer in less than 50 v/v %. This material can be organic or inorganic material with a molecular weight less than that of the base polymer. An additive can impart different properties to the polymeric material, for example, it can be a plasticizing agent, a nucleating agent, or an antioxidant.

"Blending" generally refers to mixing of a polyolefin in its pre-consolidated form with an additive. If both constituents are solid, blending can be done by using a third component such as a liquid to mediate the mixing of the two components, after which the liquid is removed by evaporating. If the additive is liquid, for example α-tocopherol, then the solid can be mixed with large quantities liquid, then diluted down to desired concentrations with the solid polymer to obtain uniformity in the blend. In the case where an additive is also an antioxidant, for example vitamin E, or α-tocopherol, then blended polymeric material is also antioxidant-doped. Polymeric material, as used herein, also applies to blends of a polyolefin and a plasticizing agent, for example a blend of UHMWPE resin powder blended with α-tocopherol and consolidated. Polymeric material, as used herein, also applies to blends of an additive, a polyolefin and a plasticizing agent, for example UHMWPE soaked in α-tocopherol.

"Plasticizing agent" refers to a what is known in the art, a material with a molecular weight less than that of the base polymer, for example α-tocopherol in polyethylene or low molecular weight polybutadiene in polyethylene, in both cases polyethylene being the base polymer. The plasticizing agent is typically added to the base polymer in less than about 20 weight percent. The plasticizing agent increases flexibility and softens the polymeric material.

The term "plasticization" or "plasticizing" refers to the properties that a plasticizing agent imparts on the polymeric material into which it has been added. There properties may include but are not limited to increased elongation at break, reduced stiffness, and increased ductility.

A "nucleating agent' refers to an additive known in the art, an organic or inorganic material with a molecular weight less than that of the base polymer, which increases the rate of crystallization in the polymeric material. Typically, organo-carboxylic acid salts, for example calcium carbonate, are good nucleation agents for polyolefins. Also, nucleating agents are typically used in small concentrations such as 0.5 wt %.

Doping:

Doping refers to a process well known in the art (see, for example, U.S. Pat. Nos. 6,448,315 and 5,827,904). In this connection, doping generally refers to contacting a polymeric material with an antioxidant under certain conditions, as set forth herein, for example, doping UHMWPE with an antioxidant under supercritical conditions. "Doping" also refers to introducing a second component into the base polymeric material in quantities less than 50 v/v %. More specifically, doping refers to introducing an antioxidant into a polymeric material, most often by diffusion of the antioxidant from a surrounding media into the polymeric material. A polymeric material treated in such a way is termed as "antioxidant-doped" polymeric material. However, the process of doping an antioxidant into a polymeric material is not limited to the diffusion process. The polymeric material can be 'doped'; however, by other additives as well, such as a plasticizing agent, in which case the polymeric material treated in such a way may be termed as 'plasticizing agent-doped'.

More specifically, for example, HPC polymeric material can be doped with an antioxidant by soaking the material in a solution of the antioxidant. This allows the antioxidant to diffuse into the polymer. For instance, the material can be soaked in 100% antioxidant. The material also can be soaked in an antioxidant solution where a carrier solvent can be used to dilute the antioxidant concentration. To increase the depth of diffusion of the antioxidant, the material can be doped for longer durations, at higher temperatures, at higher pressures, and/or in presence of a supercritical fluid.

The doping process can involve soaking of a polymeric material, medical implant or device with an antioxidant, such as vitamin E, for about an hour up to several days, preferably for about one hour to 24 hours, more preferably for one hour to 16 hours. The antioxidant can be heated to room temperature or up to about 160° C. and the doping can be carried out at room temperature or up to about 160° C. Preferably, the antioxidant can be heated to 100° C. and the doping is carried out at 100° C.

To further increase the uniformity of antioxidant in the base polymeric material, the doped polymeric material is annealed below or above the melt under ambient or high pressure. The annealing is preferably for about an hour up to several days, more preferably for about one hour to 24 hours, most preferably for one hour to 16 hours. The doped polymeric material is heated to room temperature or up to about 160° C. and the annealing is carried out at room temperature or up to about 160° C. Preferably, the doped polymeric material is heated to about 120° C. and the annealing is carried out at about 120° C.

The term "conventional UHMWPE" refers to commercially available polyethylene of molecular weights greater than about 500,000. Preferably, the UHMWPE starting material has an average molecular weight of greater than about 2 million.

By "initial average molecular weight" is meant the average molecular weight of the UHMWPE starting material, prior to any irradiation.

Cross-Linking Polymeric Material:

Polymeric Materials, for example, UHMWPE can be cross-linked by a variety of approaches, including those employing cross-linking chemicals (such as peroxides and/or silane) and/or irradiation. Preferred approaches for cross-linking employ irradiation. Cross-linked UHMWPE can be obtained according to the teachings of U.S. Pat. No. 5,879,400, PCT/US99/16070, filed on Jul. 16, 1999, PCT/US97/02220, filed Feb. 11, 1997, US Patent Publication 20030149125 (U.S. application Ser. No. 10/252,582), filed Sep. 24, 2002, and U.S. Pat. No. 6,641,617, the entirety of which are hereby incorporated by reference.

Consolidated Polymeric Material:

Consolidated polymeric material refers to a solid, consolidated bar stock, solid material machined from stock, or semi-solid form of polymeric material derived from any forms as described herein, for example, resin powder, flakes, particles, or a mixture thereof, that can be consolidated. The consolidated polymeric material also can be in the form of a slab, block, solid bar stock, machined component, film, tube, balloon, pre-form, implant, or finished medical device.

By "crystallinity" is meant the fraction of the polymer that is crystalline. The crystallinity is calculated by knowing the weight of the sample (weight in grams), the heat absorbed by the sample in melting (E, in J/g) and the heat of melting of polyethylene crystals ($\Delta H$=291 J/g), and using the following equation:

$$\% \text{ Crystallinity} = E/w \cdot \Delta H$$

By tensile "elastic modulus" is meant the ratio of the nominal stress to corresponding strain for strains as determined using the standard test ASTM 638 M III and the like or their successors.

The term "non-permanent device" refers to what is known in the art as a device that is intended for implantation in the body for a period of time shorter than several months. Some non-permanent devices could be in the body for a few seconds to several minutes, while other may be implanted for days, weeks, or up to several months. Non-permanent devices include catheters, tubing, intravenous tubing, and sutures, for example.

"Permanent device" refers to what is known in the art that is intended for implantation in the body for a period longer than several months. Permanent devices include medical devices, for example, acetabular liner, shoulder glenoid, patellar component, finger joint component, ankle joint component, elbow joint component, wrist joint component, toe joint component, bipolar hip replacements, tibial knee insert, tibial knee inserts with reinforcing metallic and polyethylene posts, intervertebral discs, sutures, tendons, heart valves, stents, and vascular grafts.

"Pharmaceutical compound", as described herein, refers to a drug in the form of a powder, suspension, emulsion, particle, film, cake, or molded form. The drug can be free-standing or incorporated as a component of a medical device.

The term "pressure chamber" refers to a vessel or a chamber in which the interior pressure can be raised to levels above atmospheric pressure.

The term "packaging" refers to the container or containers in which a medical device is packaged and/or shipped. Packaging can include several levels of materials, including bags, blister packs, heat-shrink packaging, boxes, ampoules, bottles, tubes, trays, or the like or a combination thereof. A single component may be shipped in several individual types of package, for example, the component can be placed in a bag, which in turn is placed in a tray, which in turn is placed in a box. The whole assembly can be sterilized and shipped. The packaging materials include, but not limited to, vegetable parchments, multi-layer polyethylene. Nylon 6, polyethylene terephthalate (PET), and polyvinyl chloride-vinyl acetate copolymer films, polypropylene, polystyrene, and ethylene-vinyl acetate (EVA) copolymers.

The term "heat-shrinkable packaging" refers to plastic films, bags, or tubes that have a high degree of orientation in them. Upon application of heat, the packaging shrinks down as the oriented chains retract, often wrapping tightly around the medical device.

"Melt transition temperature" refers to the lowest temperature at which all the crystalline domains in a material disappear.

"Melting point" refers to the peak melting temperature measured by a differential scanning calorimeter at a heating rate of 10° C. per minute when heating from 20° C. to 220° C.

Medical implants containing factory-assembled pieces that are in close contact with the polyethylene form interfaces. In most cases, the interfaces are not readily accessible to EtO gas or the GP during a gas sterilization process.

Irradiation:

In one aspect of the invention, the type of radiation, preferably ionizing, is used. According to another aspect of the invention, a dose of ionizing radiation ranging from about 25 kGy to about 1000 kGy is used. The radiation dose can be about 50 kGy, about 65 kGy, about 75 kGy, about 100 kGy, about 200 kGy, about 300 kGy, about 400 kGy, about 500 kGy, about 600 kGy, about 700 kGy, about 800 kGy, about 900 kGy, or about 1000 kGy, or above 1000 kGy, or any integer or fractional value thereabout or therebetween. Preferably, the radiation dose can be between about 50 kGy and about 200 kGy. These types of radiation, including x-ray, gamma and/or electron beam, kills or inactivates bacteria, viruses, or other microbial agents potentially contaminating medical implants, including the interfaces, thereby achieving product sterility. The irradiation, which may be electron or gamma irradiation, in accordance with the present invention can be carried out in air atmosphere containing oxygen, wherein the oxygen concentration in the atmosphere is at least 1%, 2%, 4%, or up to about 22%, or any integer or fractional value thereabout or therebetween. In another aspect, the irradiation can be carried out in an inert atmosphere, wherein the atmosphere contains gas selected from the group consisting of nitrogen, argon, helium, neon, or the like, or a combination thereof. The irradiation also can be carried out in a vacuum.

In accordance with a preferred feature of this invention, the irradiation may be carried out in a sensitizing atmosphere. This may comprise a gaseous substance which is of sufficiently small molecular size to diffuse into the polymer and which, on irradiation, acts as a polyfunctional grafting moiety. Examples include substituted or unsubstituted polyunsaturated hydrocarbons; for example, acetylenic hydrocarbons such as acetylene; conjugated or unconjugated olefinic hydrocarbons such as butadiene and (meth)acrylate monomers; sulphur monochloride, with chloro-tri-fluoroethylene (CTFE) or acetylene being particularly preferred. By "gaseous" is meant herein that the sensitizing atmosphere is in the gas phase, either above or below its critical temperature, at the irradiation temperature.

Metal Piece:

In accordance with the invention, the piece forming an interface with polymeric material is, for example, a metal. The metal piece in functional relation with polyethylene, according to the present invention, can be made of a cobalt chrome alloy, stainless steel, titanium, titanium alloy or nickel cobalt alloy, for example. Various metal types can also be found in U.S. Ser. No. 60/424,709, filed Nov. 8, 2002 (PCT/US03/18053, filed Jun. 10, 2003, WO 2004000159).

Non-Metallic Piece:

In accordance with the invention, the piece forming an interface with polymeric material is, for example, a non-metal. The non-metal piece in functional relation with polyethylene, according to the present invention, can be made of ceramic material, for example.

Interface:

The term "interface" in this invention is defined as the niche in medical devices formed when an implant is in a configuration where a component is in contact with another piece (such as a metallic or a non-metallic component), which forms an interface between the polymer and the metal or another polymeric material. For example, interfaces of polymer-polymer or polymer-metal are in medical prosthesis, such as orthopedic joints and bone replacement parts, for example, hip, knee, elbow or ankle replacements. Various metal/non-metal types and interfaces also can be found in U.S. Ser. No. 60/424,709, filed Nov. 8, 2002 (PCT/US03/18053, filed Jun. 10, 2003, WO 2004000159), the entirety of which is hereby incorporated by reference.

Inert Atmosphere:

The term "inert atmosphere" refers to an environment having no more than 1% oxygen and more preferably, an oxidant-free condition that allows free radicals in polymeric materials to form cross links without oxidation during a process of sterilization. An inert atmosphere is used to avoid $O_2$, which would otherwise oxidize the medical device comprising a polymeric material, such as UHMWPE. Inert atmospheric conditions such as nitrogen, argon, helium, or neon are used for sterilizing polymeric medical implants by ionizing radiation.

Inert atmospheric conditions such as nitrogen, argon, helium, neon, or vacuum are also used for sterilizing interfaces of polymeric-metallic and/or polymeric-polymeric in medical implants by ionizing radiation.

Inert atmospheric conditions also refers to a insert gas, inert fluid, or inert liquid medium, such as nitrogen gas or silicon oil.

Anoxic Environment:

"Anoxic environment" refers to an environment containing gas, such as nitrogen, with less than 21%-22% oxygen, preferably with less than 2% oxygen. The oxygen concentration in an anoxic environment also can be at least 1%, 2%, 4%, 6%, 8%, 10%, 12% 14%, 16%, 18%, 20%, or up to about 22%, or any integer or fractional value thereabout or therebetween.

Vacuum:

The term "vacuum" refers to an environment having no appreciable amount of gas, which otherwise would allow free radicals in polymeric materials to form cross links without oxidation during a process of sterilization. A vacuum is used to avoid $O_2$, which would otherwise oxidize the medical device comprising a polymeric material, such as UHMWPE.

A vacuum condition can be used for sterilizing polymeric medical implants by ionizing radiation.

A vacuum condition can be created using a commercially available vacuum pump. A vacuum condition also can be used when sterilizing interfaces of polymeric-metallic and/or polymeric-polymeric in medical implants by ionizing radiation.

Residual Free Radicals:

"Residual free radicals" refers to free radicals that are generated when a polymer is exposed to ionizing radiation such as gamma or e-beam irradiation. While some of the free radicals recombine with each other to from crosslinks, some become trapped in crystalline domains. The trapped free radicals are also known as residual free radicals.

According to one aspect of the invention, the levels of residual free radicals in the polymer generated during an ionizing radiation (such as gamma or electron beam) is preferably determined using electron spin resonance and treated appropriately to reduce the free radicals through recombination.

Sterilization:

One aspect of the present invention discloses a process of sterilization of medical implants containing polymeric material, such as cross-linked UHMWPE. The process comprises sterilizing the medical implants by ionizing sterilization with gamma or electron beam radiation, for example, at a dose level ranging from about 25-70 kGy, or by gas sterilization with ethylene oxide or gas plasma.

Another aspect of the present invention discloses a process of sterilization of medical implants containing polymeric material, such as cross-linked UHMWPE. The process comprises sterilizing the medical implants by ionizing sterilization with gamma or electron beam radiation, for example, at a dose level ranging from about 25-200 kGy. The dose level of sterilization is higher than standard levels used in irradiation. This is to allow cross-linking or further cross-linking of the medical implants during sterilization.

The term "alpha transition" refers to a transitional temperature and is normally around 90-95° C., however, in the presence of a sensitizing environment that dissolves in polyethylene, the alpha transition may be depressed. The alpha transition is believed (An explanation of the "alpha transition temperature" can be found in *Anelastic and Dielectric Effects in Polymeric Solids*, pages 141-143, by N. G. McCrum, B. E. Read and G. Williams; J. Wiley and Sons, N.Y., N.Y., published 1967) to induce motion in the crystalline phase, which is hypothesized to increase the diffusion of the sensitizing environment into this phase and/or release the trapped free radicals. Heating above the alpha transition will also increase the diffusion of the additive, such as plasticizing agent or the antioxidant into the base polymer.

The term "critical temperature" corresponds to the alpha transition of the polyethylene. The term "below melting point" or "below the melt" refers to a temperature below the melting point of a polyethylene, for example, UHMWPE. The term "below melting point" or "below the melt" refers to a temperature less than 155° C., which may vary depending on the melting temperature of the polyethylene. The term "above melting point" or "above the melt" refers to a temperature above the melting point of a polyethylene, for example, UHMWPE. The term "above melting point" or "above the melt" refers to a temperature more than 145° C., which may vary depending on the melting temperature of the polyethylene. The melting temperature of the polyethylene can be, for example, 155° C., 145° C., 140° C. or 135° C., which again depends on the properties of the polyethylene being treated, for example, extended chain crystals, crystallinity, molecular weight averages and ranges, batch variations, etc. For example, "above melting point" or "above the melt" of a polymeric material under high pressure during a high-pressure crystallization process refers to a temperature at or above 150° C. The melting temperature is typically measured using a differential scanning calorimeter (DSC) at a heating rate of 10° C. per minute. The peak melting temperature thus measured is referred to as melting point and occurs, for example, at approximately 137° C. for some grades of UHMWPE. It may be desirable to conduct a melting study on the starting polyethylene material in order to determine the melting temperature and to decide upon an irradiation and annealing temperature.

The term "annealing" refers to heating the polymer above or below its peak melting point. Annealing time can be at least 1 minute to several weeks long. In one aspect the annealing time is about 4 hours to about 48 hours, preferably 24 to 48 hours and more preferably about 24 hours. The annealing time required to achieve a desired level of recovery following mechanical deformation is usually longer at lower annealing temperatures. "Annealing temperature" refers to the thermal condition for annealing in accordance with the invention.

The term "contacted" includes physical proximity with or touching such that the sensitizing agent can perform its intended function. Preferably, a polyethylene composition or pre-form is sufficiently contacted such that it is soaked in the sensitizing agent, which ensures that the contact is sufficient. Soaking is defined as placing the sample in a specific environment for a sufficient period of time at an appropriate temperature, for example, soaking the sample in a solution of an antioxidant. The environment is heated to a temperature ranging from room temperature to a temperature below the melting point of the material. The contact period ranges from at least about 1 minute to several weeks and the duration depending on the temperature of the environment.

The term "oxidation-resistant" refers to a state of polymeric material having an oxidation index (A. U.) of less than about 0.5 following aging polymeric materials for 5 weeks in air at 80° C. oven. Thus, an oxidation-resistant cross-linked polymeric material generally shows an A. U. of less than about 0.5 after the aging period.

"Oxidation index" refers to the extent of oxidation in polymeric material. Oxidation index is calculated by obtaining an infrared spectrum for the polymeric material and analyzing the spectrum to calculate an oxidation index, as the ratio of the areas under the $1740 cm^{-1}$ carbonyl and $1370 cm^{-1}$ methylene stretching absorbances after subtracting the corresponding baselines.

The term "Mechanical deformation" refers to deformation taking place below the melting point of the material, essentially 'cold-working' the material. The deformation modes include uniaxial, channel flow, uniaxial compression, biaxial compression, oscillatory compression, tension, uniaxial tension, biaxial tension, ultra-sonic oscillation, bending, plane stress compression (channel die) or a combination of any of the above. The deformation could be static or dynamic. The dynamic deformation can be a combination of the deformation modes in small or large amplitude oscillatory fashion. Ultrasonic frequencies can be used. All deformations can be performed in the presence of sensitizing gases and/or at elevated temperatures.

The term "deformed state" refers to a state of the polyethylene material following a deformation process, such as a mechanical deformation, as described herein, at solid or at melt. Following the deformation process, deformed polyethylene at a solid state or at melt is be allowed to solidify/crystallize while still maintains the deformed shape or the newly acquired deformed state.

"IBMA" refers to irradiation below the melt and mechanical annealing. "IBMA" also is referred to as "CIMA" (Cold Irradiation and Mechanically Annealed).

Sonication or ultrasonic at a frequency range between 10 and 100 kHz can be used, with amplitudes on the order of 1-50 microns. The time of sonication is dependent on the frequency and temperature of sonication. In one aspect, sonication or ultrasonic frequency ranged from about 1 second to about one week, preferably about 1 hour to about 48 hours, more preferably about 5 hours to about 24 hours and yet more preferably about 12 hours.

The invention is further described by the following examples, which do not limit the invention in any manner.

EXAMPLES

Example 1

Electron Beam Irradiation of Polyethylene for Sterilization or Cross-Linking

Blocks or rods of UHMWPE were machined into 1 cm thick pieces. These samples were irradiated using a 2.5 MeV van de Graff generator (e-beam) at Massachusetts Institute of Technology by passing under the electron beam multiple times to achieve the desired radiation dose level (approximately 12.5 kGy per pass).

Example 2

Gamma Irradiation of Polyethylene for Sterilization or Cross-Linking

Compression molded blocks (5.5×10×12 cm) were gamma irradiated using a $Co^{60}$ source (Steris Isomedix, Northborough, Mass.).

Example 3

Blending with Vitamin E Powder and Irradiation Above the Melting Point of UHMWPE UHMWPE blocks blended with 0, 0.05, 0.1, 0.3 and 1.0 wt/wt % vitamin E are irradiated to 0, 65, 100, 150 and 200-kGy by gamma or e-beam irradiation above the melting point of UHMWPE, at about 170° C.

Example 4

Irradiation Followed by High Pressure Crystallization by Route I and Route II

Compression molded GUR1050 UHMWPE blocks (5.5× 10×12 cm) were gamma irradiated to 65 kGy in air.

Route I: One 2" dia. cylinder was machined from an irradiated block and placed in a pressure chamber, where it was heated to 200° C. in water and held for 5 hours. Then, the pressure was increased to 380 MPa and the sample was held at this temperature and pressure for 5 hours. Finally, the sample was cooled to room temperature and the pressure was subsequently released.

Route II: Another 2" dia. cylinder was placed in a pressure chamber, where it was pressurized to 380 MPa in water first, then heated to 200° C. and held for 5 hours. Finally, the sample was cooled to room temperature and the pressure was subsequently released.

Differential scanning colarimetry (DSC) was used to measure the crystallinity of the polyethylene test samples. The DSC specimen was weighed with a Sartorius CP 225D balance to a resolution of 0.01 milligrams and placed in an aluminum sample pan. The pan was crimped with an aluminum cover and placed in a TA instruments Q-1000 Differential Scanning calorimeter. The sample and the reference were then heated at a heating rate of 10° C./min from −20° C. to 160° C., cooled to −20° C. and subjected to another heating cycle from −20° C. to 160° C. at 10° C./min. Heat flow as a function of time and temperature was recorded and the cycles are referred to as $1^{st}$ heat, $1^{st}$ cool and $2^{nd}$ heat, respectively.

Crystallinity was determined by integrating the enthalpy peak from 20° C. to 160° C., and normalizing it with the enthalpy of melting of 100% crystalline polyethylene, 291 J/g.

Dogbone specimens were tested to determine mechanical properties per ASTM D-638 using a MTS II machine (Eden Prarie, Minn.) at a crosshead speed of 10 mm/min.

Figure 3:
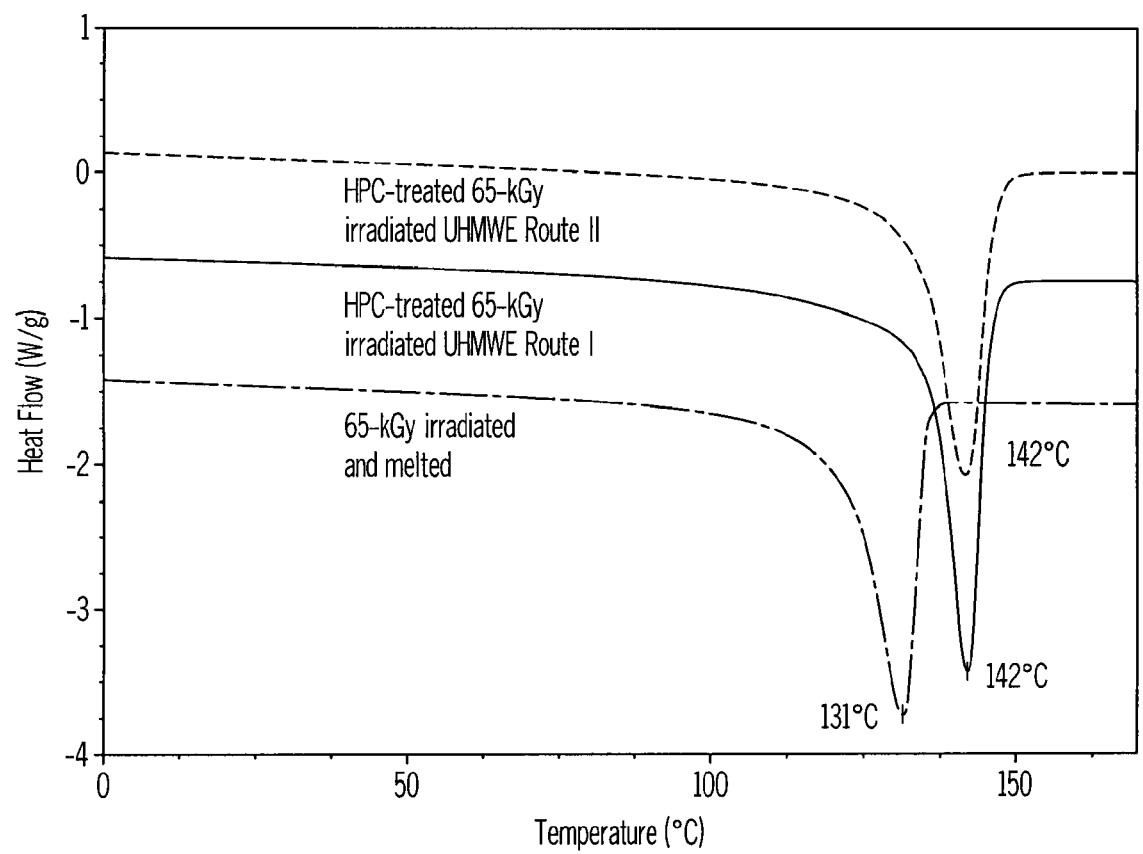
FIG. 3 shows DSC analysis of HPC treated cross-linked polyethylene obtained through Route I and Route II treatments compared to non-HPC treated cross-linked UHMWPE.
Figure 4A:
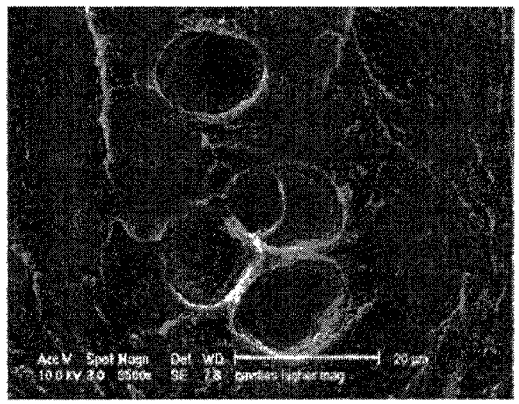
FIG. 4 (A-D) depict SEM images of freeze fracture surfaces of high pressure crystallized virgin (a), 0.1 wt % (b), 0.3 wt % (c), 1.0 wt % α-tocopherol-blended UHMWPE.
Figure 4B:
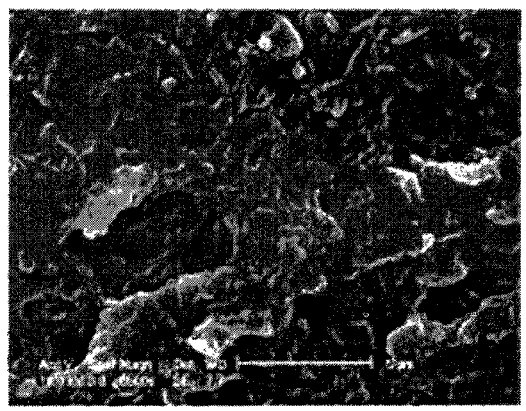
Figure 4C:
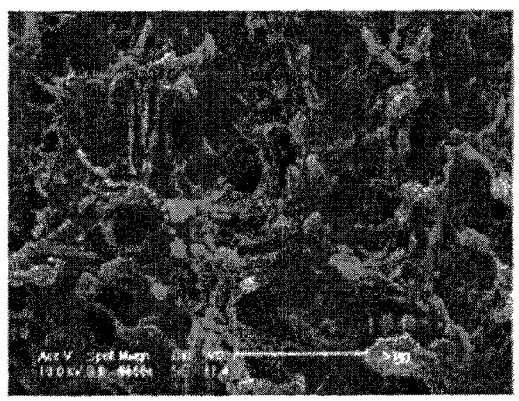
Figure 4D:
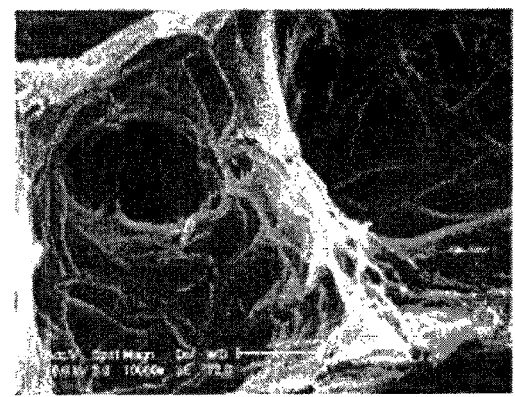
Figure 5A:
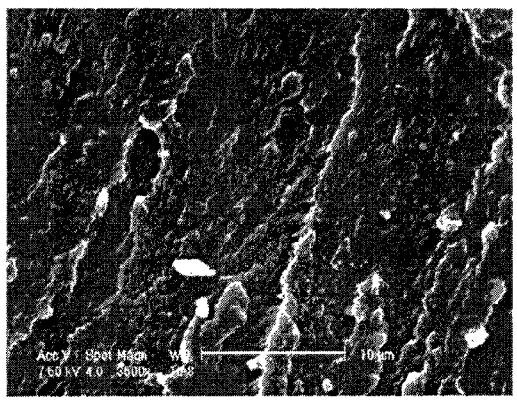
FIG. 5 (A-D) illustrate SEM images of freeze fracture surfaces of virgin (a), 0.1 wt % (b), 0.3 wt % (c), 1.0 wt % α-tocopherol-blended UHMWPE.
Figure 5B:
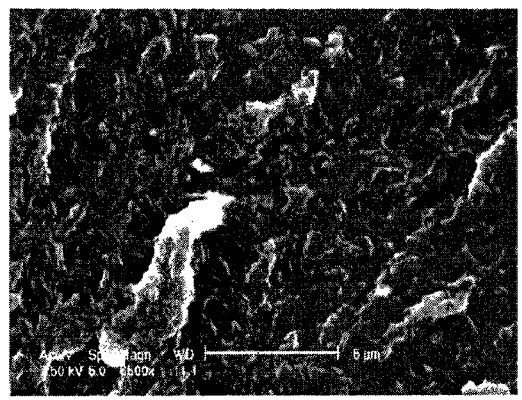
Figure 5C:
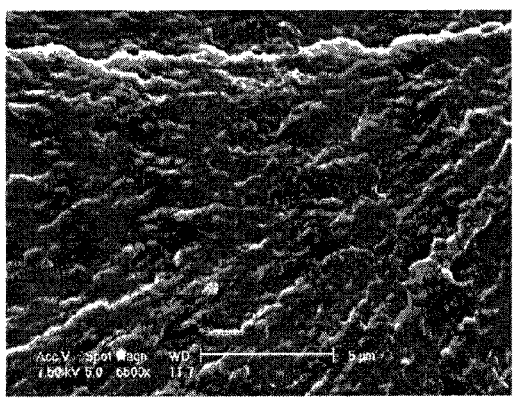
Figure 5D:
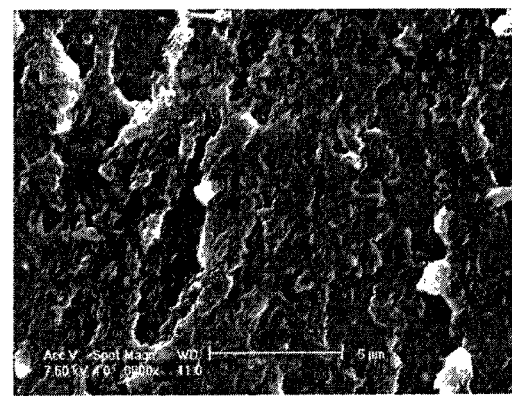

Route II resulted in the formation of extended chain crystals. The DSC analysis showed the presence of high temperature (142° C.) melting crystals in the 65-kGy irradiated and HPC treated polyethylene, using both Route I and Route II (see FIG. 3). The increase in peak melting temperature from 132° C. to 142° C. indicates the formation of extended chain crystals for irradiated UHMWPE during HPC treatment. The crystallinity of 65-kGy irradiated polyethylene was 57±1%, which increased to 63±1% after Route I HPC treatment, and to 59±2% after Route II HPC treatment.

Irradiated and HPC-treated UHMWPE by Route I had no detectable free radicals. Irradiated and HPC-treated UHMWPE by Route II had reduced or no detectable free radicals.

The mechanical properties of 65-kGy irradiated HPC-treated UHMWPEs are reported in Table 1.

TABLE 1

Tensile mechanical properties of UHMWPE.

| | WF (kJ/m$^2$) | UTS (MPa) | EAB (%) |
| --- | --- | --- | --- |
| 65-kGy HPC Route I | 1474 ± 65 | 48 ± 2 | 246 ± 11 |
| 65-kGy HPC Route II | 1631 ± 423 | 47 ± 8 | 301 ± 22 |

Example 5

Wear Rate of HPC-Treated Vitamin E-Blended UHMWPE

Ram extruded GUR1050 UHMWPE was used as control. GUR1050 UHMWPE powder was mixed with vitamin E (D,L-α-tocopherol, >98%) to 5 wt/wt %. Then, the mixture was diluted with UHMWPE powder to 0.1 wt/wt % vitamin E in UHMWPE. The mixture was compression molded into blocks (5.5×10×12 cm), which were machined to 2" diameter before high pressure crystallization (HPC). HPC was carried out in a custom-built one liter high pressure chamber. A 2" dia. cylinder was placed in the pressure chamber, where it was heated to 180° C. in water and held for 5 hours. Then, the pressure was increased to 310 MPa and the sample was held at this temperature and pressure for 5 hours. Finally, the sample was cooled to room temperature and the pressure was subsequently released. As controls, virgin UHMWPE, 0.1 wt % blended UHMWPE, virgin UHMWPE HPC-treated in the same manner were used.

Pins machined from the above described samples (diameter 9 mm, length 13 mm, n≥3) were tested on a custom-built bi-directional POD wear tester at a frequency of 2 Hz. Bovine calf serum was used as lubricant and quantified wear gravimetrically at 0.5 million-cycle intervals until 2 million cycles (MC).

HPC treated 0.1 wt % vitamin-E/UHMWPE blend showed significantly lower wear than the virgin UHMWPE while HPC treatment in the absence of vitamin E increased the wear rate of UHMWPE (see Table 2).

TABLE 2

Wear rate of virgin and HPC treated UHMWPEs.

| | Wear rate (mg/MC) |
| --- | --- |
| Virgin | 7.4 ± 2.2 |
| HPC | 13.4 ± 0.4 |
| 0.1 wt % HPC | 5.1 ± 1.1 |

Example 6

Mechanical Properties of HPC-Treated, Vitamin E-Blended UHMWPE

Ram extruded GUR1050 UHMWPE was used as control. GUR1050 UHMWPE powder was mixed with vitamin E (D,L-α-tocopherol, >98%) to 5 wt/wt %. Then, the mixture was diluted with UHMWPE powder to 0.1, 0.3, and 1.0 wt/wt % vitamin E in UHMWPE. The mixture was compression molded into blocks (5.5×10×12 cm), which were machined to 2" diameter before high pressure crystallization (HPC). HPC was carried out in a custom-built one liter high pressure chamber, A 2" dia. cylinder was placed in the pressure chamber, where it was heated to 180° C. in water and held for 5 hours. Then, the pressure was increased to 310 MPa and the sample was held at this temperature and pressure for 5 hours. Finally, the sample was cooled to room temperature and the pressure was subsequently released. As controls, virgin UHMWPE, and virgin UHMWPE HPC-treated in the same manner were used.

Differential scanning colarimetry (DSC) was used to measure the crystallinity of the polyethylene test samples. The DSC specimen was weighed with a Sartorius CP 225D balance to a resolution of 0.01 milligrams and placed in an aluminum sample pan. The pan was crimped with an aluminum cover and placed in a TA instruments Q-1000 Differential Scanning calorimeter. The sample and the reference were then heated at a heating rate of 10° C./min from −20° C. to 160° C., cooled to −20° C. and subjected to another heating cycle from −20° C. to 160° C. at 10° C./min. Heat flow as a function of time and temperature was recorded and the cycles are referred to as $1^{st}$ heat, $1^{st}$ cool and $2^{nd}$ heat, respectively.

Crystallinity was determined by integrating the enthalpy peak from 20° C. to 160° C., and normalizing it with the enthalpy of melting of 100% crystalline polyethylene, 291 J/g.

Dogbone specimens were tested to determine mechanical properties per ASTM D-638 using a MTS II machine (Eden Prarie, Minn.) at a crosshead speed of 10 mm/min.

The crystallinity of UHMWPE was improved from 70% to 76% with the addition of 0.1 wt % vitamin E. No significant difference was noted in the crystallinity of high pressure crystallized polyethylenes that had been blended with higher concentrations of Vitamin E (p>0.1, see Table 3).

The ultimate tensile strength of 0.1 wt % vitamin E blended, high pressure crystallized UHMWPE was significantly higher than virgin, high pressure crystallized (HPC) UHMWPE (p=0.012, Table 3), which was not true at higher concentrations of vitamin E.

TABLE 3

Tensile mechanical properties of UHMWPEs.

|  | EAB (%) | Crystallinity (%) | UTS (MPa) | YS (MPa) | WF (kJ/m$^2$) |
|---|---|---|---|---|---|
| Untreated | | | | | |
| Virgin | 484 ± 29 | 59 ± 2 | 51 ± 3 | 21 ± 1 | 2589 ± 156 |
| HPC treated | | | | | |
| Virgin | 361 ± 31 | 70 ± 1 | 56 ± 6 | 24 ± 2 | 2281 ± 392 |
| 0.1 wt % | 373 ± 11 | 76 ± 1 | 66 ± 2 | 28 ± 1 | 3219 ± 186 |
| 0.3 wt % | 376 ± 25 | 76 ± 1 | 50 ± 6 | 25 ± 3 | 1905 ± 348 |
| 1.0 wt % | 391 ± 23 | 74 ± 2 | 51 ± 3 | 24 ± 2 | 2020 ± 223 |

The synergistic effect of vitamin E and HPC on UHMWPE at a vitamin E concentration of 0.1 wt/wt %, resulted not only in low wear, but also in a 'super-tough' UHMWPE with very high work-to-failure (Table 3).

Example 7

Morphological Characterization of HPC-Treated, Vitamin E-Blended UHMWPEs

Ram extruded GUR1050 UHMWPE was used as control. GUR1050 UHMWPE powder was mixed with vitamin E (D,L-α-tocopherol, >98%) to 5 wt/wt %. Then, the mixture was diluted with UHMWPE powder to 0.1, 0.3, and 1.0 wt/wt % vitamin E in UHMWPE. The mixture was compression molded into blocks (5.5×10×12 cm), which were machined to 2" diameter before high pressure crystallization (HPC). HPC was carried out in a custom-built one liter high pressure chamber. A 2" dia. cylinder was placed in the pressure chamber, where it was heated to 180° C. in water and held for 5 hours. Then, the pressure was increased to 310 MPa and the sample was held at this temperature and pressure for 5 hours. Finally, the sample was cooled to room temperature and the pressure was subsequently released. As controls, virgin UHMWPE, and virgin UHMWPE HPC-treated in the same manner were used.

Freeze-fractured surfaces were gold-coated (Edward Sputtercoater S150B) and electron microscopy images were obtained by using a FEI/Phillips XL30 FEG ESEM (Hillsboro, Oreg.).

SEM images revealed abundant voids in all HPC-treated samples except 0.1 wt % vitamin E-blended sample (see FIGS. 4 (a-d)), which were not observed in any of the non-HPC-treated samples (see FIGS. 5 (a-d)). The cavities might have formed as a result of melting and re-crystallization of larger crystals under pressure or displacement of vitamin E during recrystallization. There appear to be competing mechanisms where effects of higher crystallinity are balanced out by the effects of voids at around 0.1 wt % vitamin E concentration.

Example 8

Doping and Homogenization of HPC-Treated UHMWPE

Ram extruded GUR1050 UHMWPE was used. A 2" dia. cylinder was placed in the pressure chamber, where it was heated to 180° C. in water and held for 5 hours. Then, the pressure was increased to 310 MPG (45,000 psi) and the sample was held at this temperature and pressure for 5 hours. Finally, the sample was cooled to room temperature and the pressure was subsequently released. This 2" diameter high pressure crystallized block was machined into 1 cm-thick sections and irradiated at room temperature by electron-beam irradiation to 125 kGy using a 2.5 MeV van de Graff generator at Massachusetts Institute of Technology by passing under the beam multiple times to achieve the desired dose (approximately 12.5 kGy per pass).

One 1 cm-thick section was cut in two. One piece was doped with α-tocopherol at 120° C. for 5 hours, it was then taken out of α-tocopherol, coiled down to room temperature, wiped clean with cotton gauze and placed in a convection oven at 120° C. for 64 hours. The other piece was doped with α-tocopherol at 124° C. for 5 hours, it was then taken out of α-tocopherol, cooled down to room temperature, wiped clean with cotton gauze and placed in a convection oven at 124° C. for 64 hours.

The α-tocopherol profiles in these two samples were measured by infrared spectroscopy as described in Example 9. The samples were cut in half and sectioned (150 μm). Infrared spectra were collected by a BioRad UMA 500 microscope with an aperture size of 50×50 μm as a function of depth away from the free surface of the original sample.

An α-tocopherol index was calculated as the ratio of the areas under the 1265 cm$^{-1}$ α-tocopherol and 1895 cm$^{-1}$ polyethylene skeletal absorbances.

Figure 6:
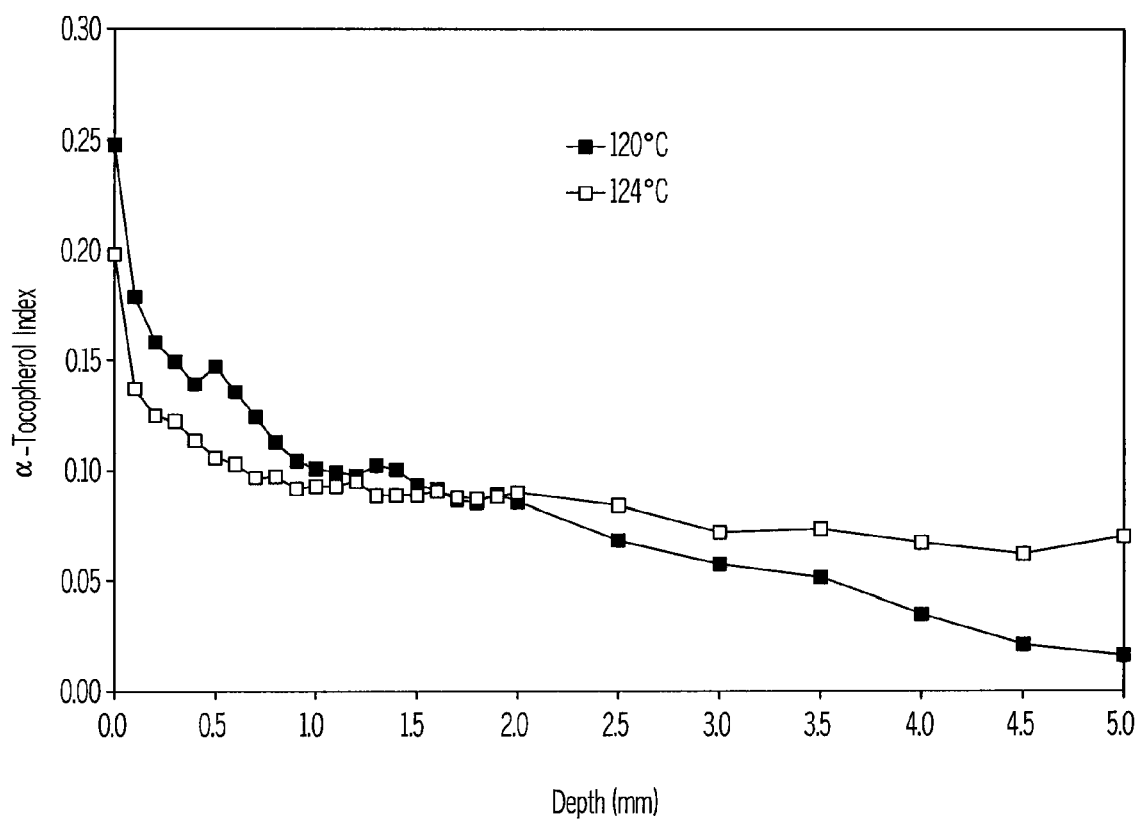
FIG. 6 shows α-tocopherol profiles in high pressure crystallized, irradiated, α-tocopherol doped and homogenized UHMWPE. The graph shows the region from the surface to the center of the sample, where the concentration of α-tocopherol is lowest.
Figure 7:
FIG. 7 depicts a TEM image of 0.1 wt % Vitamin E-blended HPC UHMWPE.

The α-tocopherol profiles of high pressure crystallized, 125 kGy irradiated, α-tocopherol-doped and homogenized UHMWPE samples are shown in FIG. 6. The lowest index level attained in the sample doped and annealed at 120° C. was 0.016 and the lowest index level attained in the sample doped and annealed at 124° C. was 0.069.

Example 9

Measurement of Antioxidant Diffusion into Polyethylene

To measure the diffusion profile of the antioxidant in the test samples that were doped in α-tocopherol, a cross-section was cut out of the doped section (100-150 μm) using an LKB Sledge Microtome. The thin cross-section was then analyzed using a BioRad UMA 500 infrared microscope (Natick, Mass.). Infrared spectra were collected with an aperture size of 50×50 μm as a function of depth away from one of the edges that coincided with the free surface of the sample that contacted the antioxidant during immersion. The absorbance between 1226 and 1295 cm$^{-1}$ is characteristic of α-tocopherol and polyethylene does not absorb near these frequencies. For polyethylene, the 1895 cm$^{-1}$ wave number for the CH$_2$ rocking mode is a typical choice as an internal reference. The normalized value, which is the ratio of the integrated absorbances of 1260 cm$^{-1}$ and 1895 cm$^{-1}$, is an index that provides a relative metric of α-tocopherol composition in polyethylene and is known as the α-tocopherol (vitamin E) index.

Example 10

Blending Followed by High Pressure Crystallization by Route II Followed by Irradiation Followed by High Pressure Crystallization by Route I Ram extruded GUR1050 UHMWPE is used as control. GUR1050 UHMWPE powder is mixed with vitamin E (D,L-

α-tocopherol, >98%) to 5 wt/wt %. Then, the mixture is diluted with UHMWPE powder to 0.1 wt/wt % vitamin E in UHMWPE. The mixture is compression molded into blocks (5.5×10×12 cm), which are machined to 2" diameter before high pressure crystallization (HPC). HPC is carried out in a custom-built one liter high pressure chamber. A 2" dia. cylinder is placed in the pressure chamber, where the pressure is increased to 310 MPa (45,000 psi) in water and then heated to 180° C. The block is held at this temperature and pressure for 5 hours. Finally, the sample is cooled to room temperature and the pressure is subsequently released. The high pressure crystallized block is irradiated to 100-kGy. Then it is placed in the high pressure chamber, where it is heated to 180° C. in water and held for 5 hours. Then the pressure is increased to 310 MPa (45,000 psi) and the sample is held at this temperature and pressure for 5 hours. Finally, the sample is cooled to room temperature and the pressure is subsequently released.

Example 11

Blending Followed by High Pressure Crystallization by Route II Followed by Irradiation Followed by High Pressure Crystallization by Route II Ram extruded GUR1050 UHMWPE is used as control. GUR1050 UHMWPE powder is mixed with vitamin E (D,L-α-tocopherol, >98%) to 5 wt/wt %. Then, the mixture is diluted with UHMWPE powder to 0.1 wt/wt % vitamin E in UHMWPE. The mixture is compression molded into blocks (5.5×10×12 cm), which are machined to 2" diameter before high pressure crystallization (HPC). HPC is carried out in a custom-built one liter high pressure chamber. A 2" dia. cylinder is placed in the pressure chamber, where the pressure is increased to 310 MPa (45,000 psi) in water and then heated to 180° C. The block is held at this temperature and pressure for 5 hours. Finally, the sample is cooled to room temperature and the pressure is subsequently released. The high pressure crystallized block is irradiated to 100-kGy. Then it is placed in the pressure chamber, where the pressure is increased to 310 MPa (45,000 psi) in water and then heated to 180° C. The block is held at this temperature and pressure for 5 hours. Finally, the sample is cooled to room temperature and the pressure is subsequently released.

Example 12

Wear Rate of Vitamin E-Blended, Irradiated and High Pressure Crystallized UHMWPE Ram extruded GUR1050 UHMWPE is used as control. GUR1050 UHMWPE powder is mixed with vitamin E (D,L-α-tocopherol, >98%) to 5 wt/wt %. Then, the mixture is diluted with UHMWPE powder to 0.1 wt/wt % vitamin E in UHMWPE. The mixture is compression molded into blocks (5.5×10×12 cm), which are machined to 2" diameter before high pressure crystallization (HPC). HPC is carried out in a custom-built one liter high pressure chamber. A 2" dia. cylinder is placed in the pressure chamber, where it is heated to 200° C. in water and held for 5 hours. Then, the pressure is increased to 380 MPa (55,000 psi) and the sample is held at this temperature and pressure for 5 hours. Finally, the sample is cooled to room temperature and the pressure is subsequently released.

Pins machined from the above described samples (diameter 9 mm, length 13 mm, n≥3) are tested on a custom-built bi-directional POD wear tester at a frequency of 2 Hz. We use bovine calf serum as lubricant and quantify wear gravimetrically at 0.5 million-cycle intervals until 2 million cycles (MC).

By using high pressure crystallization on vitamin E-blended cross-linked UHMWPE, a wear-resistant UHMWPE is obtained.

Example 13

Improved Mechanical Strength of High Pressure Crystallized, Slow-Irradiated and Melted UHMWPE Ram extruded GUR1050 UHMWPE was used as stock. A 2" dia. cylinder was placed in the pressure chamber, where it was heated to 180° C. in water and held for 5 hours. Then, the pressure was increased to 310 MPa (45,000 psi) and the sample was held at this temperature and pressure for 5 hours. Finally, the sample was cooled to room temperature and the pressure was subsequently released. This 2" diameter high pressure crystallized block was machined into 1 cm-thick sections and irradiated at room temperature by electron-beam irradiation to 150 kGy using a 2.5 MeV van de Graff generator at Massachusetts Institute of Technology by passing under the beam multiple times to achieve the desired dose (approximately 12.5 kGy per pass). One 1 cm-thick section was irradiated to 150 kGy at approximately 4 kGy/pass. One 1 cm-thick section irradiated to 150 kGy at 12.5 kGy/pass was melted at 170° C. in vacuum after irradiation.

Dogbone specimens were tested to determine mechanical properties per ASTM D-638 using a MTS II machine (Eden Prarie, Minn.) at a crosshead speed of 10 mm/min.

The ultimate tensile strength of irradiated samples was reduced compared to high pressure crystallized samples (see Table 4). However, both slow irradiation and melting after irradiation increased the strength of irradiated HPC UHMWPE.

TABLE 4

Crystallinity and mechanical strength of high pressure crystallized and irradiated UHMWPEs

| Sample | Crystallinity (%) | UTS (MPa) |
|---|---|---|
| Conventional UHMWPE | 61 ± 2 | 51 ± 5 |
| HPC UHMWPE | 75 ± 2 | 56 ± 6 |
| 150-kGy irradiated HPC UHMWPE | 79 ± 1 | 28 ± 4 |
| 150-kGy irradiated HPC UHMWPE and melted | 59 ± 1 | 36 ± 1 |
| 150-kGy irradiated HPC UHMWPE (slow irradiation) | — | 36 |
| 100 kGy irradiated and melted UHMWPE (CISM) | 58 ± 1 | 28 ± 2 |

This effect is due to the tie molecules between crystallites being placed under tension after HPC; and during irradiation of the tie-molecules. As a result, they became more prone to chain scission under tension. This tensioning would then adversely affect the fracture of the tie-molecules during mechanical testing. Both slow irradiation and melting allowed these taut-tie molecules to relax, improving mechanical strength.

Example 14

Improved Mechanical Strength of High Pressure Crystallized, Slow-Irradiated and Annealed UHMWPE Ram extruded GUR1050 UHMWPE is used as stock. A 2" dia. cylinder was placed in the pressure chamber, where it is heated to 180° C. in water and held for 5 hours. Then, the pressure is increased to 310 MPa (45,000 psi) and the sample is held at this temperature and pressure for 5 hours. Finally, the sample is cooled to room temperature and the pressure is subsequently released. The 2" diameter high pressure crystallized block is machined into 1 cm-thick sections and irradiated at room temperature by electron-beam irradiation to 150 kGy using a 2.5 MeV van de Graff generator at Massachusetts Institute of Technology by passing under the beam multiple times to achieve the desired dose (approximately 4 kGy per pass). One cm-thick sections irradiated to 150 kGy are thermally annealed at 100° C., 120° C. and 136° C. in vacuum after irradiation to improve mechanical properties.

Example 15

Vitamin E

Vitamin E (Acros™ 99% D-α-Tocopherol, Fisher Brand), was used in the experiments described herein, unless otherwise specified. The vitamin E used is very light yellow in color and is a viscous fluid at room temperature. Its melting point is 2-3° C.

Example 16

Bi-Directional Pin-on-Disk (POD) Wear Testing

The wear rate was quantified on a number of UHMWPE test samples that were subjected to various processing steps as described in some of the examples below. For this, the wear behavior of the UHMWPE sample was tested using cylindrical shaped samples (9 mm diameter and 13 mm height) on a custom-built bi-directional pin-on-disk (POD) wear tester at a frequency of 2 Hz. Bovine calf serum was used as lubricant and quantified wear gravimetrically at 0.5 million-cycle intervals. Initially, the pins were subjected to 200,000 cycles of POD testing to remove reach a steady state wear rate independent of diffusion or asperities on the surface. Three pins from each group were tested for a total of 2 million cycles. The wear rate was calculated as the linear regression of wear vs. number of cycles from 0.2 to 2 million cycles.

Example 17

Determination of Crystallinity with Differential Scanning Calorimetry

The crystallinity was quantified on a number of UHMWPE test samples that were subjected to various processing steps as described in some of the examples below. For this, differential scanning colarimetry (DSC) was used to measure the crystallinity of the polyethylene test samples. The DSC specimens were weighed with a Sartorius CP 225D balance to a resolution of 0.01 milligrams and placed in an aluminum sample pan. The pan was crimped with an aluminum cover and placed in a TA instruments Q-1000 Differential Scanning Calorimeter. The samples and the reference were then heated at a heating rate of 10° C./min from −20° C. to 160° C., cooled to −20° C. and subjected to another heating cycle from −20° C. to 160° C. at 10° C./min. Heat flow as a function of time and temperature was recorded and the cycles are referred to as $1^{st}$ heat, $1^{st}$ cool and $2^{nd}$ heat, respectively.

Crystallinity was determined by integrating the enthalpy peak from 20° C. to 160° C., and normalizing it with the enthalpy of melting of 100% crystalline polyethylene, 291 J/g.

Example 18

Dimensional Stability of Irradiated and High Pressure Crystallized (Route II) Acetabular Liner An acetabular liner machined of 100-kGy irradiated and melted GUR1050 UHMWPE was placed in a pressure chamber, where it was pressurized to 380 MPa (55,000 psi) in water first, then heated to 200° C. and held for 5 hours. Finally, the sample was cooled to room temperature and the pressure was subsequently released.

The dimensions of the liner were measured by a coordinate measuring machine (CMM, Global A2, Brown & Sharpe, North Kingstown R1) before and after high pressure crystallization. Table 5 shows that the dimensional changes on the articular and backsides of the liner were minimal because melting was avoided. Overall, this HPC-treated liner was very stable.

TABLE 5

Dimensional stability of a 100-kGy irradiated and melted acetabular liner high pressure crystallized at 55,000 psi and 200° C. by Route II.

| | Inner Diameter (mm) | Outer Diameter (mm) |
|---|---|---|
| Pre-HPC | 36.128 ± 0.000 | 42.275 ± 0.001 |
| Post-HPC | 36.099 ± 0.002 | 42.231 ± 0.003 |
| Change | −0.029 | −0.044 |

Example 19

Morphological Characterization of UHMWPE Blended with 0.1 wt % α-Tocopherol and High Pressure Crystallized by Route I by Transmission Electron Microscopy (TEM)

Ram extruded GUR1050 UHMWPE was used as control. GUR1050 UHMWPE powder was mixed with vitamin E (D,L-α-tocopherol, >98%) to 5 wt/wt %. Then, the mixture was diluted with UHMWPE powder to 0.1 wt/wt % vitamin E in UHMWPE. The mixture was compression molded into blocks (5.5×10×12 cm), which were machined to 2" diameter before high pressure crystallization (HPC). HPC was carried out in a custom-built one liter high pressure chamber. A 2" dia. cylinder was placed in the pressure chamber, where it was heated to 200° C. in water and held for 5 hours. Then, the pressure was increased to 380 MPa (55,000 psi) and the sample was held at this temperature and pressure for 5 hours. Finally, the sample was cooled to room temperature and the pressure was subsequently released.

A sample cut from the highly crystalline bar was etched by heating in chlorosulfonic acid at 60° C. for 6 hours, washed in sulfuric acid and water. It was microtomed, stained with a uranyl acetate solution and imaged at 100 kV accelerating voltage on a Philips 420T.

0.1 wt % α-tocopherol blended and high pressure crystallized UHMWPE clearly exhibited the presence of 'extended chain crystals'.

It is to be understood that the description, specific examples and data, while indicating exemplary embodiments, are given by way of illustration and are not intended to limit the present invention. Various changes and modifications within the present invention will become apparent to the skilled artisan from the discussion, disclosure and data contained herein, and thus are considered part of the invention.

The invention claimed is:

1. A method of making a cross-linked and interlocked hybrid material for a medical device or implant, wherein the method comprises:
   a) mixing a polymeric material with an antioxidant to form a polymeric blend;
   b) compression molding of the polymeric blend to the counterface of second material, thereby forming an interlocked hybrid material having an interface between the polymeric blend and the second material;
   c) elevating the temperature of the interlocked hybrid material to about 80° C. to below the melting point of the polymeric blend; and
   d) irradiating the interlocked hybrid material from step (c) by electron beam radiation at the elevated temperature that is between about 80° C. to below the melting point of the polymeric blend, thereby forming cross-links in the polymeric blend and yielding a cross-linked and interlocked hybrid material for a medical device or implant, wherein: (i) the cross-linking strengthens the polymeric blend to minimize separation at the interface, (ii) the antioxidant provides resistance to post-irradiation oxidation, and (iii) the irradiation sterilizes the interface.

2. The method according to claim 1, wherein the second material is porous so as to permit bony in-growth into the medical device or implant.

3. The method according to claim 2, wherein the second material is metallic.

4. The method according to claim 2, wherein the second material is non-metallic.

5. The method according to claim 1, wherein the polymeric material is ultrahigh molecular weight polyethylene.

6. The method according to claim 1, wherein the antioxidant is an α-tocopherol.

7. A method of making a medical device or implant comprising a cross-linked and interlocked hybrid material, wherein the method comprises:
   a) mixing a polymeric material with an antioxidant to form a polymeric blend;
   b) compression molding of the polymeric blend to the counterface of second material, thereby forming an interlocked hybrid material having an interface between the polymeric blend and the second material;
   c) elevating the temperature of the interlocked hybrid material to about 80° C. to below the melting point of the polymeric blend;
   d) irradiating the interlocked hybrid material from step (c) by electron beam radiation at the elevated temperature that is between about 80° C. to below the melting point of the polymeric blend, thereby forming cross-links in the polymeric blend and yielding a cross-linked and interlocked hybrid material for a medical device or implant, wherein: (i) the cross-linking strengthens the polymeric blend to minimize separation at the interface, (ii) the antioxidant provides resistance to post-irradiation oxidation, and (iii) the irradiation sterilizes the interface; and
   e) machining the cross-linked and interlocked hybrid material to form the medical device or implant.

8. The method according to claim 7, further comprising the step of e) sterilizing the medical device or implant.

9. The method according to claim 8, wherein the sterilizing is by gas sterilization.

10. The method according to claim 8, wherein the sterilizing is by ionizing radiation, wherein the antioxidant provides resistance to post-sterilization oxidation.

11. The method according to claim 7, wherein the second material is porous so as to permit bony in-growth into the medical device or implant.

12. The method according to claim 11, wherein the second material is metallic.

13. The method according to claim 11, wherein the second material is non-metallic.

14. The method according to claim 7, wherein the polymeric material is ultrahigh molecular weight polyethylene.

15. The method according to claim 7, wherein the antioxidant is an α-tocopherol.

16. A method of making a cross-linked polymeric material for a medical device or implant, wherein the method comprises:
   a) mixing a polymeric material with an antioxidant to form a polymeric blend;
   b) elevating the temperature of the polymeric blend to about 80° C. to below the melting point of the polymeric blend; and
   c) irradiating the polymeric blend from step (b) by electron beam radiation at the elevated temperature that is between about 80° C. to below the melting point of the polymeric blend, thereby forming cross-links in the polymeric blend and yielding a cross-linked polymeric blended material for a medical device or implant, wherein: (i) the cross-linking increases wear resistance, and (ii) the antioxidant provides resistance to post-irradiation oxidation.

17. The method according to claim 16, wherein the polymeric material is ultrahigh molecular weight polyethylene.

18. The method according to claim 16, wherein the antioxidant is an α-tocopherol.

19. The method according to claim 16, wherein the polymeric blend is consolidated prior to the irradiation step.

20. A method of making a medical device or implant comprising a cross-linked polymeric material, wherein the method comprises:
   a) mixing a polymeric material with an antioxidant to form a polymeric blend;
   b) consolidating the polymeric blend;
   c) elevating the temperature of the consolidated polymeric blend to about 80° C. to below the melting point of the polymeric blend;
   d) irradiating the consolidated polymeric blend from step (c) by electron beam radiation at the elevated temperature that is between about 80° C. to below the melting point of the polymeric blend, thereby forming cross-links in the consolidated polymeric blend and yielding a cross-linked consolidated polymeric blended material for a medical device or implant, wherein: (i) the cross-linking increase wear resistance, and (ii) the antioxidant provides resistance to post-irradiation oxidation; and
   e) machining the cross-linked consolidated polymeric material to form the medical device or implant.

21. The method according to claim 20, further comprising the step of d) sterilizing the medical device or implant.

22. The method according to claim 21, wherein the sterilizing is by gas sterilization.

23. The method according to claim 21, wherein the sterilizing is by ionizing radiation, wherein the antioxidant provides resistance to post-sterilization oxidation.

24. The method according to claim 20, wherein the polymeric material is ultrahigh molecular weight polyethylene.

25. The method according to claim 20, wherein the antioxidant is an α-tocopherol.

26. The method of making a cross-linked and interlocked hybrid material for a medical device or implant, wherein the method comprises:
  a) mixing a polymeric material with an antioxidant to form a polymeric blend;
  b) compression molding of the polymeric blend to the counterface of second material, thereby forming an interlocked hybrid material having an interface between the polymeric blend and the second material;
  c) elevating the temperature of the interlocked hybrid material to above room temperature to below 90° C.; and
  d) irradiating the interlocked hybrid material from step (c) by electron beam radiation at the elevated temperature that is between above room temperature to below 90° C., thereby forming cross-links in the polymeric blend and yielding a cross-linked and interlocked hybrid material for a medical device or implant, wherein: (i) the cross-linking strengthens the polymeric blend to minimize separation at the interface, (ii) the antioxidant provides resistance to post-irradiation oxidation, and (iii) the irradiation sterilizes the interface.

27. The method according to claim 26, wherein the second material is porous so as to permit bony in-growth into the medical device or implant.

28. The method according to claim 27, wherein the second material is metallic.

29. The method according to claim 27, wherein the second material is non-metallic.

30. The method according to claim 26, wherein the polymeric material is ultrahigh molecular weight polyethylene.

31. The method according to claim 26, wherein the antioxidant is an α-tocopherol.

32. A method of making a medical device or implant comprising a cross-linked and interlocked hybrid material, wherein the method comprises:
  a) mixing a polymeric material with an antioxidant to form a polymeric blend;
  b) compression molding of the polymeric blend to the counterface of second material, thereby forming an interlocked hybrid material having an interface between the polymeric blend and the second material;
  c) elevating the temperature of the interlocked hybrid material to above room temperature to below 90° C.;
  d) irradiating the interlocked hybrid material from step (c) by electron beam radiation at the elevated temperature that is between above room temperature to below 90° C., thereby forming cross-links in the polymeric blend and yielding a cross-linked and interlocked hybrid material for a medical device or implant, wherein: (i) the cross-linking strengthens the polymeric blend to minimize separation at the interface, (ii) the antioxidant provides resistance to post-irradiation oxidation, and (iii) the irradiation sterilizes the interface; and
  e) machining the cross-linked and interlocked hybrid material to form the medical device or implant.

33. The method according to claim 32, further comprising the step of e) sterilizing the medical device or implant.

34. The method according to claim 33, wherein the sterilizing is by gas sterilization.

35. The method according to claim 33, wherein the sterilizing is by ionizing radiation, wherein the antioxidant provides resistance to post-sterilization oxidation.

36. The method according to claim 32, wherein the second material is porous so as to permit bony in-growth into the medical device or implant.

37. The method according to claim 36, wherein the second material is metallic.

38. The method according to claim 36, wherein the second material is non-metallic.

39. The method according to claim 32, wherein the polymeric material is ultrahigh molecular weight polyethylene.

40. The method according to claim 32, wherein the antioxidant is an α-tocopherol.

41. A method of making a cross-linked polymeric material for a medical device or implant, wherein the method comprises:
  a) mixing a polymeric material with an antioxidant to form a polymeric blend;
  b) elevating the temperature of the polymeric blend to above room temperature to below 90° C.; and
  c) irradiating the polymeric blend from step (b) by electron beam radiation at the elevated temperature that is between above room temperature to below 90° C., thereby forming cross-links in the polymeric blend and yielding a cross-linked polymeric blended material for a medical device or implant, wherein: (i) the cross-linking increases wear resistance, and (ii) the antioxidant provides resistance to post-irradiation oxidation.

42. The method according to claim 41, wherein the polymeric material is ultrahigh molecular weight polyethylene.

43. The method according to claim 41, wherein the antioxidant is an α-tocopherol.

44. The method according to claim 41, wherein the polymeric blend is consolidated prior to the irradiation step.

45. A method of making a medical device or implant comprising a cross-linked polymeric material, wherein the method comprises:
  a) mixing a polymeric material with an antioxidant to form a polymeric blend;
  b) consolidating the polymeric blend;
  c) elevating the temperature of the consolidated polymeric blend to above room temperature to below 90° C.;
  d) irradiating the consolidated polymeric blend from step (c) by electron beam radiation at the elevated temperature that is between above room temperature to below 90° C., thereby forming cross-links in the consolidated polymeric blend and yielding a cross-linked consolidated polymeric blended material for a medical device or implant, wherein: (i) the cross-linking increase wear resistance, and (ii) the antioxidant provides resistance to post-irradiation oxidation; and
  e) machining the cross-linked consolidated polymeric material to form the medical device or implant.

46. The method according to claim 45, further comprising the step of d) sterilizing the medical device or implant.

47. The method according to claim 46, wherein the sterilizing is by gas sterilization.

48. The method according to claim 46, wherein the sterilizing is by ionizing radiation, wherein the antioxidant provides resistance to post-sterilization oxidation.

49. The method according to claim 45, wherein the polymeric material is ultrahigh molecular weight polyethylene.

50. The method according to claim 45, wherein the antioxidant is an α-tocopherol.

* * * * *